US011180760B2

(12) United States Patent
Zack et al.

(10) Patent No.: US 11,180,760 B2
(45) Date of Patent: Nov. 23, 2021

(54) IDENTIFICATION OF MOLECULAR PATHWAYS AND METHODS OF USE THEREOF FOR TREATING RETINAL NEURODEGENERATION AND OTHER NEURODEGENERATIVE DISORDERS

(71) Applicant: THE JOHNS HOPKINS UNIVERSITY, Baltimore, MD (US)

(72) Inventors: Donald J. Zack, Baltimore, MD (US); Derek S. Welsbie, Lutherville-Timonium, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/383,982

(22) PCT Filed: Mar. 11, 2013

(86) PCT No.: PCT/US2013/030203
§ 371 (c)(1),
(2) Date: Sep. 9, 2014

(87) PCT Pub. No.: WO2013/134766
PCT Pub. Date: Sep. 12, 2013

(65) Prior Publication Data
US 2015/0030572 A1 Jan. 29, 2015

Related U.S. Application Data

(60) Provisional application No. 61/609,026, filed on Mar. 9, 2012.

(51) Int. Cl.
*C12N 15/113* (2010.01)
*A61K 31/713* (2006.01)
*C12Q 1/48* (2006.01)
*C12Q 1/6883* (2018.01)
*A61K 31/553* (2006.01)

(52) U.S. Cl.
CPC ........ *C12N 15/1137* (2013.01); *A61K 31/553* (2013.01); *A61K 31/713* (2013.01); *C12Q 1/485* (2013.01); *C12Q 1/6883* (2013.01); *C12N 2310/14* (2013.01); *C12N 2320/30* (2013.01); *C12Q 2600/136* (2013.01); *C12Y 207/10* (2013.01); *C12Y 207/11* (2013.01); *C12Y 207/99* (2013.01); *G01N 2500/04* (2013.01)

(58) Field of Classification Search
None
See application file for complete search history.

(56) References Cited

U.S. PATENT DOCUMENTS

2006/0014165 A1* 1/2006 Hakonarson ........... A61K 31/47
435/6.16
2007/0254850 A1* 11/2007 Lieberman ......... C12N 15/1136
514/44 A
2009/0023676 A1* 1/2009 McSwiggen ........... A61K 47/54
514/44 R
2010/0056609 A1* 3/2010 DiAntonio ........... A61K 31/415
514/44 A
2012/0328609 A1* 12/2012 Lewcock ........... A61K 31/7105
424/133.1

FOREIGN PATENT DOCUMENTS

WO 2010017541 A1 2/2010
WO 2011050192 A1 4/2011
WO 2011119777 A1 9/2011

OTHER PUBLICATIONS

Miller et al., A dual leucine kinase-dependent axon self-destruction program promotes Wallerian degeneration, Nature Neuroscience vol. 12 [ No. 4 [ Apr. 2009.*
Canola et al., Retinal Stem Cells Transplanted into Models of Late Stages of Retinitis Pigmentosa Preferentially Adopt a Glial or a Retinal Ganglion Cell Fate, Invest Ophthalmol Vis Sci. 2007;48:446-454) DOI:10.1167/iovs.06-0190.*
Itoh et al., ZPK/DLK, a Mitogen-Activated Protein Kinase Kinase Kinase, Is a Critical Mediator of Programmed Cell Death of Motoneurons, The Journal of Neuroscience, May 18, 2011 • 31(20):7223-7228 • 7223.*
Ballios et al., Biology and therapeutic potential of adult retinal stem cells, Can J Ophthalmol 2010;45:342-51.*
Collins et al., Highwire Restrains Synaptic Growth by Attenuating a MAP Kinase Signal, Neuron 51, 57-69, Jul. 6, 2006.*
Nihalani et al., Identification of Structural and Functional Domains in Mixed Lineage Kinase Dual Leucine Zipper-bearing Kinase Required for Complex Formation and Stress-activated Protein Kinase Activation, The Journal of Biological Chemistry, vol. 275, No. 10, Issue of Mar. 10, pp. 7273-7279, 2000.*
Sakuma et al., Molecular Cloning and Functional Expression of a cDNA Encoding a New Member of Mixed Lineage Protein Kinase from Human Brain, The Journal of Biological Chemistry, vol. 272, No. 45, Issue of Nov. 7, pp. 28622-28629, 1997.*
Jackson et al., Expression profiling reveals off-target gene regulation by RNAi, Nature Biotechnology, Brief Communications, May 18, 2003 (Year: 2003).*
Fakhr et al., Precise and efficient siRNA design: a key point in competent gene silencing, Cancer Gene Therapy (2016) 23, 73-82, (Year: 2016).*
Written Opinion dated Jun. 21, 2013 from PCT International Application No. PCT/US2013/030203.
Beirowski et al., "The WldS gene delays axonal but not somatic degeneration in a rat glaucoma model." Eur J Neurosci. Sep. 2008; 28(6):1166-79.

(Continued)

*Primary Examiner* — Louise W Humphrey
*Assistant Examiner* — Srikanth Patury
(74) *Attorney, Agent, or Firm* — Casimir Jones, S.C.; Thomas A. Isenbarger

(57) ABSTRACT

Drug targets, pathways, kits and methods for treating conditions related to neurodegeneration or ocular disease, are disclosed.

6 Claims, 10 Drawing Sheets

(56) References Cited

OTHER PUBLICATIONS

Chen et al., "Leucine Zipper-bearing Kinase promotes axon growth in mammalian central nervous system neurons." Sci Rep. Aug. 11, 2016; 6:31482.

Dickson et al., "POSH is an intracellular signal transducer for the axon outgrowth inhibitor Nogo66." J Neurosci. Oct. 6, 2010; 30(40):13319-25.

Ghosh et al., "DLK induces developmental neuronal degeneration via selective regulation of proapoptotic JNK activity." J Cell Biol. Sep. 5, 2011; 194(5):751-64.

Ghosh-Roy et al., "Calcium and cyclic AMP promote axonal regeneration in Caenorhabditis elegans and require DLK-1 kinase." J Neurosci. Mar. 3, 2010; 30(9):3175-83.

Hirai et al., "The c-Jun N-terminal kinase activator dual leucine zipper kinase regulates axon growth and neuronal migration in the developing cerebral cortex." J Neurosci. Nov. 15, 2006; 26(46):11992-2002.

Libby et al., "Susceptibility to neurodegeneration in a glaucoma is modified by Bax gene dosage." PLoS Genet. Jul. 2005; 1(1):17-26.

Sakuma et al., "Molecular cloning and functional expression of a cDNA encoding a new member of mixed lineage protein kinase from human brain." J Biol Chem. Nov. 7, 1997; 272(45):28622-9.

Yang et al., "Pathological axonal death through a MAPK cascade that triggers a local energy deficit." Cell. Jan. 15, 2015;160(1-2):161-76.

\* cited by examiner

IDENTIFICATION OF MOLECULAR PATHWAYS AND METHODS OF USE THEREOF FOR TREATING RETINAL NEURODEGENERATION AND OTHER NEURODEGENERATIVE DISORDERS

RELATED APPLICATIONS

This application is a 35 U.S.C. § 371 National Stage Entry of International Application No. PCT/US2013/030203 having an international filing date of Mar. 11, 2013, which claims the benefit of priority to U.S. Provisional Application No. 61/609,026, filed Mar. 9, 2012, the entire disclosure of which are incorporated herein in their entirety.

FEDERALLY SPONSORED RESEARCH OR DEVELOPMENT

This invention was made with government support under 5R21EY019737 and 1K08EY022078 and awarded by the National Institutes of Health. The government has certain rights in the invention.

BACKGROUND

Neurodegenerative disorders afflict numerous patients throughout the world and can be devastating to patients and caregivers. Such disorders also can result in great financial burdens, with annual costs currently exceeding several hundred billion dollars in the United States alone. Current treatments for such disorders often are inadequate. Further, many such disorders are age-related, and thus their incidence is rapidly increasing as demographics trend toward an aging population. One such disease, glaucoma, results in damage to the optic nerve and is a major cause of vision loss and blindness, especially in the elderly. Although various treatments for glaucoma exist, many such treatments are of limited efficacy and/or have significant side effects. Reduction of intraocular pressure, generally through pharmacologic or surgical intervention, is presently the mainstay of glaucoma therapy. Such therapies, however, often are only partially effective and generally cannot restore neuronal cell function once such function has been lost. Other examples include retinal degeneration, such as retinitis pigmentosa and the atrophic ("dry") form of age-related macular degeneration (dAMD), which are types of retinal neurodegeneration that can cause significant visual loss and blindness and currently are essentially untreatable.

SUMMARY

The presently disclosed subject matter describes the identification of pathways, drug targets, and biomarkers related to retinal degenerative diseases including, but not limited to, glaucoma, photoreceptor degeneration, such as retinitis pigmentosa and age-related degeneration, and describes the modulation of these targets as approaches for treating retinal and other neurodegeneration.

In one aspect, the presently disclosed subject matter describes a method for inhibiting or preventing retinal ganglion cell injury or death, the method comprising contacting the retinal ganglion cell with a small molecule that modulates protein kinase expression or activity. Examples of the protein kinase include MAP3K12 (also known as DLK), MAP3K13, MAP3K14, MAP2K7, MAP2K4, LYN, PLK3, PFKP MARK3, MARK2, TAOK1, IKBKB, BRSK2, PBK, PRKCH, TESK1, Csnk1e, Oxsr1, Tgfbr2, Mapk10, PFTK1, ERN2, AK2, HSPB8, FRAP1, DGUOK, ERN1, STK32B, PIK3C2G, BCR, DYRK1A, DYRK1B, PNCK, EIF2AK1, PKD2L1, NRK, Endothelin Receptor Type B, and TLK2. The modulation of protein kinase activity or expression may be an inhibition or increase in protein kinase activity or expression. In one aspect, the small molecule is a short interfering or silencing RNA (siRNA). In a further aspect, the siRNA targets MAP3K12, MAP3K13, MAP2K4, or MAP2K7. In another aspect, the small molecule is selected from the group consisting of CEP-1347 and CEP-11004.

In another aspect, the presently disclosed subject matter provides a method for preventing or treating an ocular neurodegenerative disease in a subject in need thereof, the method comprising administering to the subject a therapeutically effective amount of a small molecule which modulates protein kinase expression and/or activity. Examples of the protein kinase include MAP3K12, MAP3K13, MAP3K14, MAP2K7, MAP2K4, LYN, PLK3, PFKP, MARK3, MARK2, TAOK1, IKBKB, BRSK2, PBK, PRKCH, TESK1, Csnk1e, Oxsr1, Tgfbr2, Mapk10, PFTK1, ERN2, AK2, HSPB8, FRAP1, DGUOK, ERN1, STK32B, PIK3C2G, BCR, DYRK1A, DYRK1B, PNCK, EIF2AK1, PKD2L1, NRK, Endothelin Receptor Type B, and TLK2. In one aspect, the small molecule is a siRNA that targets MAP3K12, MAP3K13, MAP2K4, or MAP2K7. In another aspect, the small molecule is selected from the group consisting of CEP-1347 and CEP-11004.

In a further aspect, the presently disclosed subject matter provides a method for identifying injury of a neuron or retinal pigment epithelial (RPE) cell, the method comprising measuring the amount of expression or activity of a target protein kinase in the neuron or RPE cell; and determining if the amount of protein kinase expression or activity in the neuron or RPE cell is greater than the amount of protein kinase expression or activity in a control neuron or RPE cell; wherein a determination that the amount of protein kinase expression or activity is greater in the neuron or RPE cell compared to the control neuron or RPE cell is indicative of injury in the neuron. In a particular aspect, the target protein kinase is selected from the group consisting of MAP3K12, MAP3K13, MAP2K4, and MAP2K7. In another particular aspect, the neuron and control neuron are retinal ganglion cells or photoreceptor cells.

In a still further aspect, the presently disclosed subject matter provides a method for identifying a gene encoding a protein kinase associated with neuronal or retinal pigment epithelial (RPE) cell injury or death. In one aspect, the method comprises: providing a neuron or RPE cell; contacting the neuron or RPE cell with at least one silencing RNA (siRNA) targeting a protein kinase in an amount sufficient to inhibit or increase kinase activity of the protein kinase; and determining whether the neuron or RPE cell survives; wherein a determination that the neuron or RPE cell survives is an indication that the gene encoding the protein kinase is associated with neuronal or RPE cell injury or death. In a particular aspect, the target protein kinase is selected from the group consisting of MAP3K12, MAP3K13, MAP2K4, and MAP2K7. In another particular aspect, the neuron is a retinal ganglion cell or a photoreceptor cell.

BRIEF DESCRIPTION OF THE FIGURES

Figure 2:
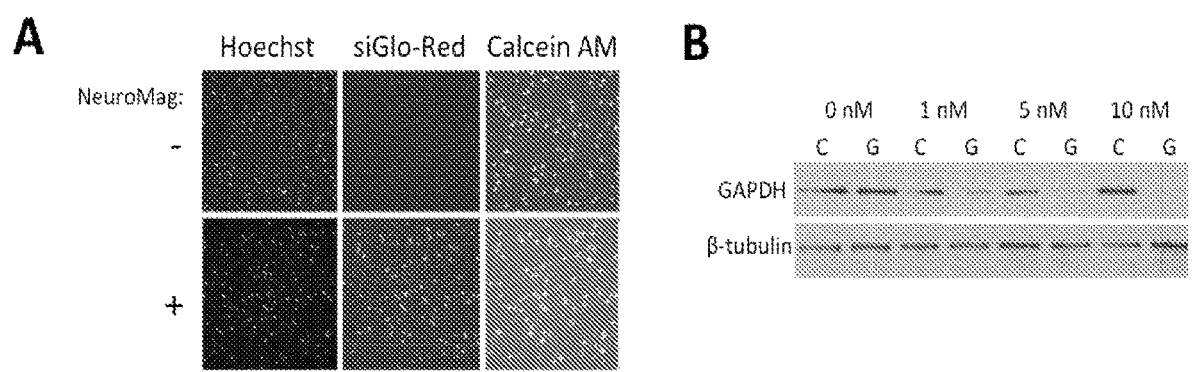
Figure 4:
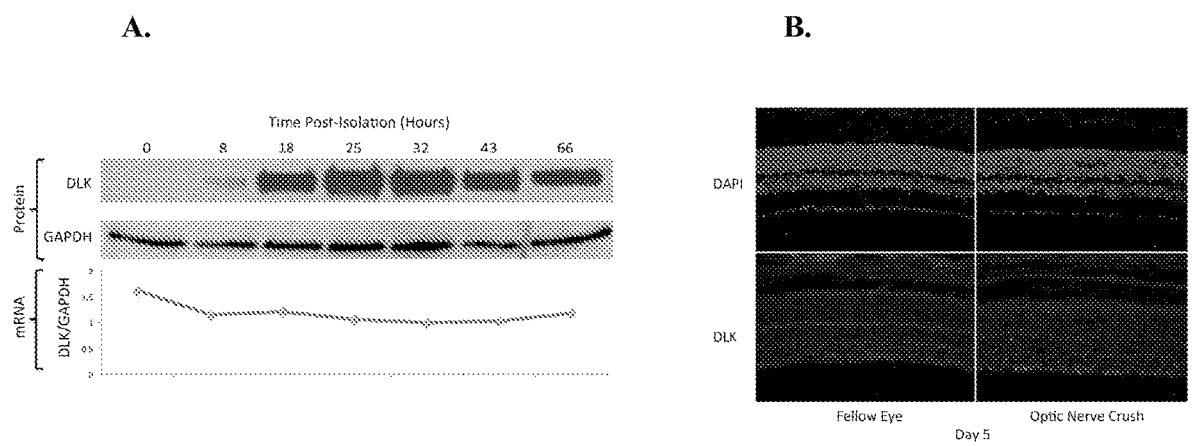
Figure 5:
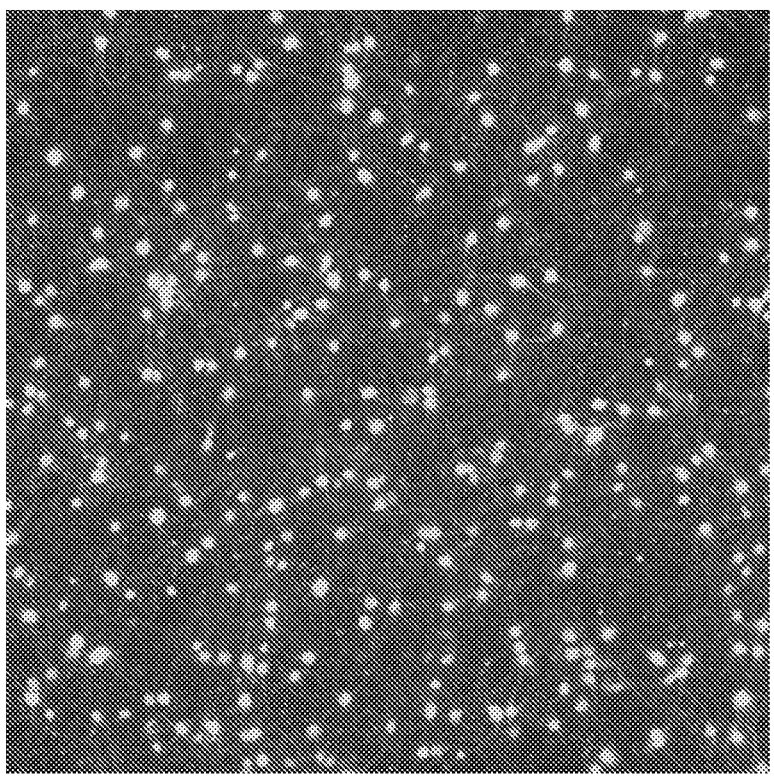
Figure 7:
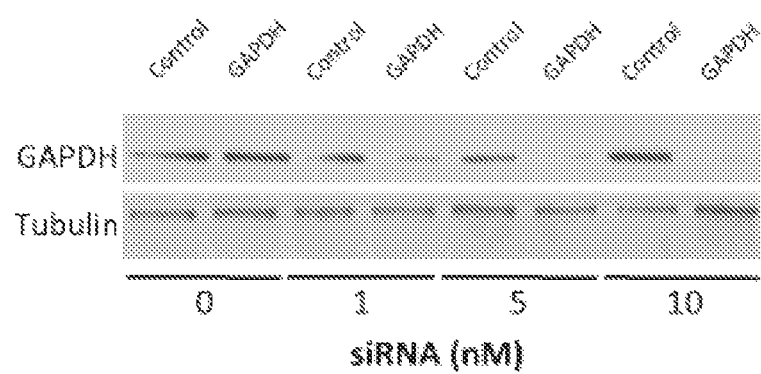
Figure 8:
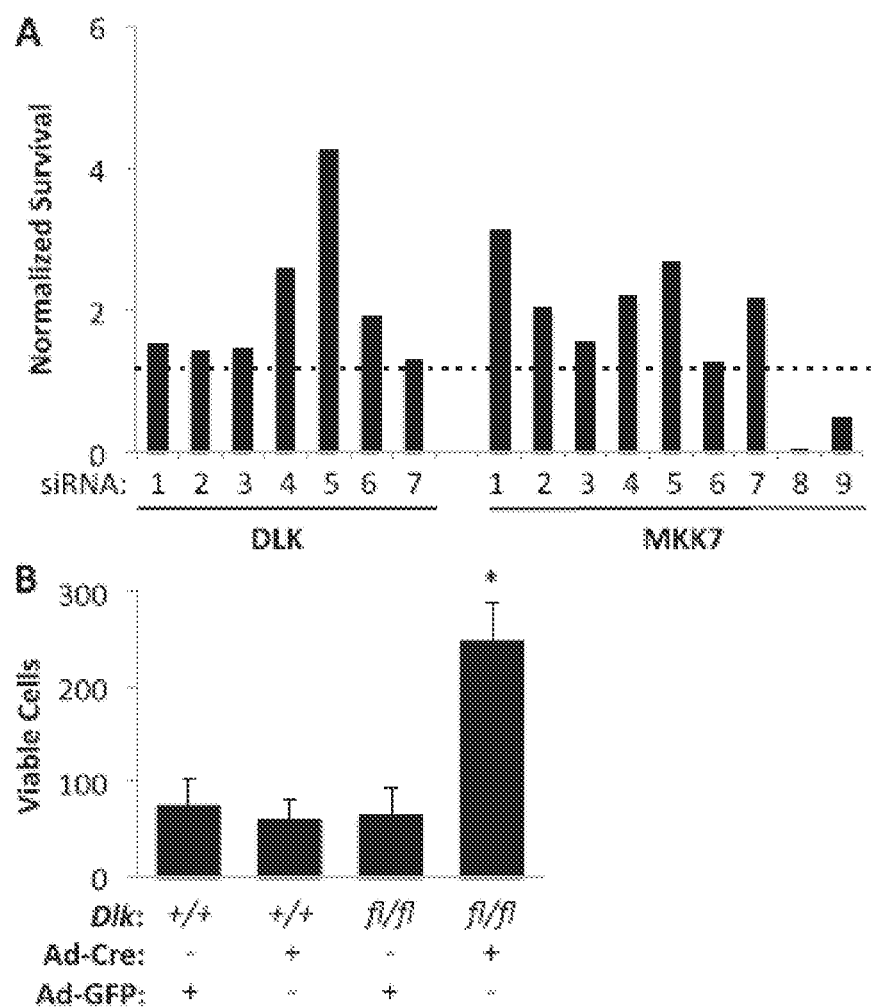
Figure 9:
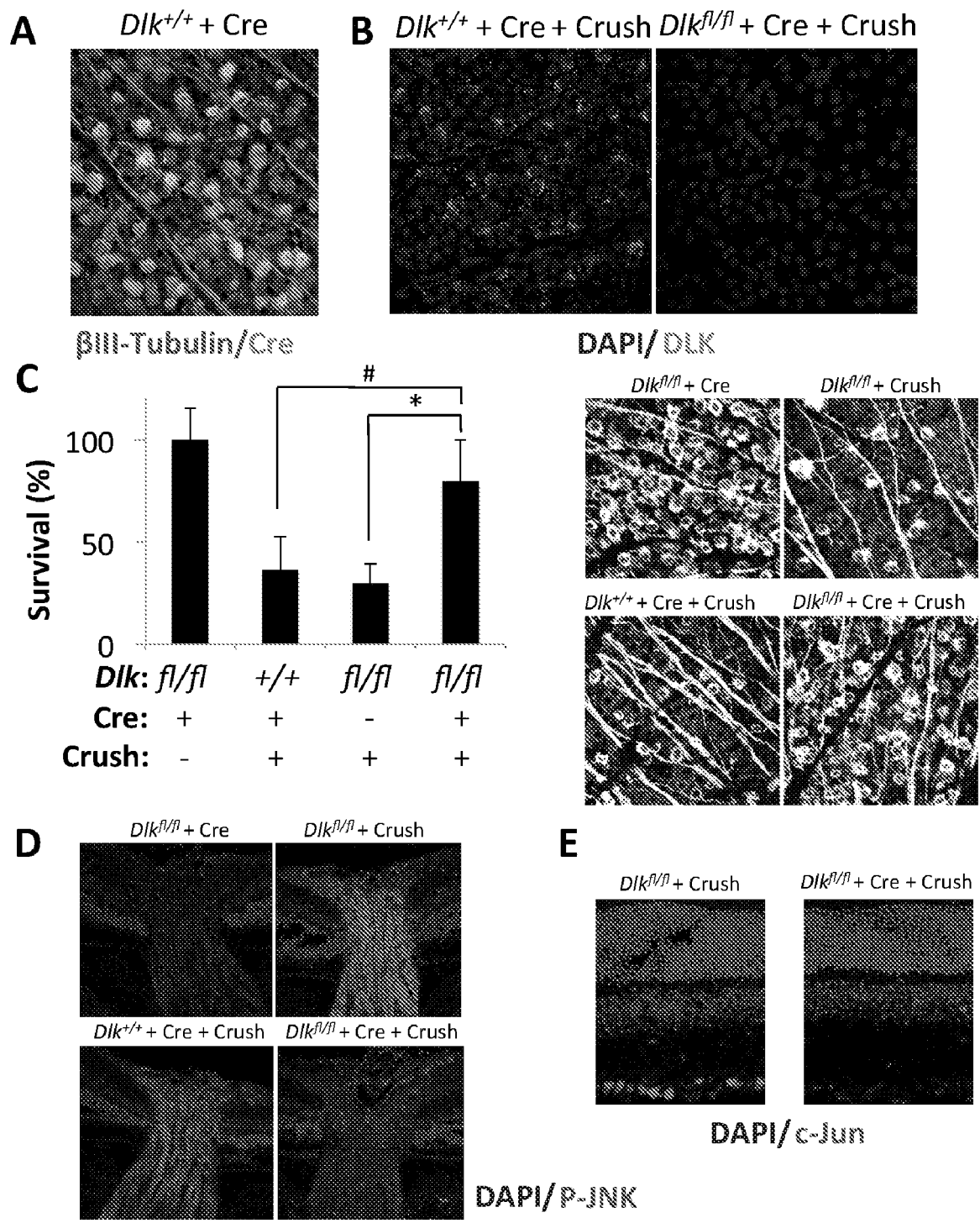
Figure 10:
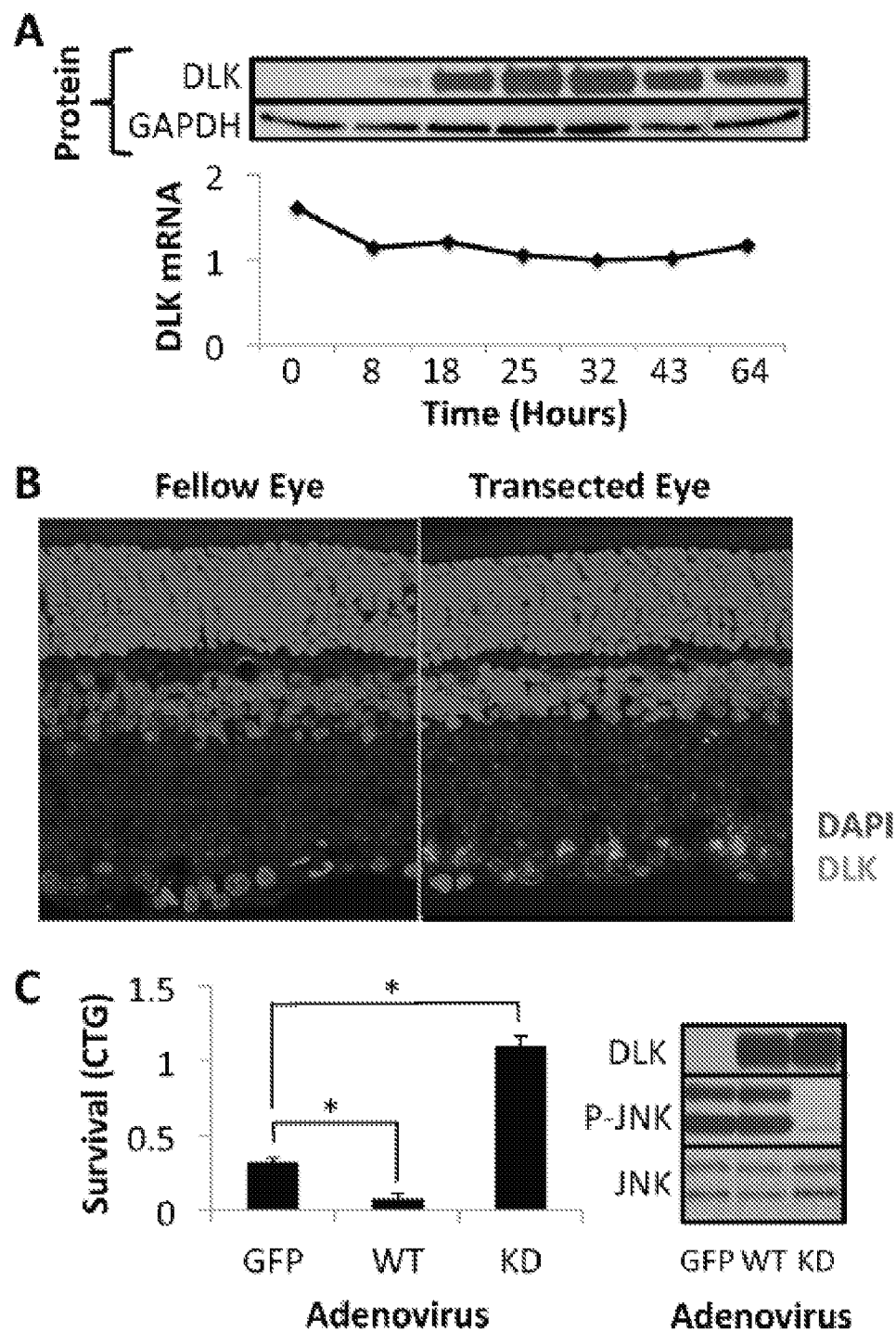

Having thus described the presently disclosed subject matter in general terms, reference will now be made to the accompanying Figures, which are not necessarily drawn to scale, and wherein:

FIGS. 1A-1D show that broad-spectrum kinase inhibitors, sunitinib and VX680, are neuroprotective to primary retinal ganglion cells (RGCs) in vitro and in vivo: (A) primary RGCs plated in neurotrophin-depleted media and stained with calcein AM at 72 hours in the absence or presence of 1 μM sunitinib; (B) survival of primary RGCs in response to increasing doses of sunitinib and VX680; (C and D) RGC survival in C57Bl/6 mice after injection intravitreally with 1 μL of drug-eluting microspheres containing 0.125, 0.25, or 0.5 mg/mL of sunitinib;

FIGS. 2A and 2B show knockdown in primary RGCs using magnetofection-based siRNA delivery: (A) RGCs were transfected at the time of isolation with 20-nM siGLO-red with (bottom) or without (top) NeuroMag and stained for viability at 24 hours with calcein AM; and (B) RGCs were transfected with increasing amounts of siRNA against GAPDH (G) or a nontargeting control (C) and immunoblotted for GAPDH or β-tubulin expression at 48 hours;

FIGS. 3A-3F show the screening of a kinase-enriched siRNA library in primary RGCs to identify a validated neuroprotective target: (A) RGCs were plated in 96-well format and transfected with 2112 siRNAs (20 nM) targeting 704 genes. Survival at 72 hours for any given well was normalized to the mean of the 6 control wells (defined as 1.0); (B) shown are the top three siRNA candidates; (C) confirmation screen using an independent set of siGenome or On-Target plus siRNAs; (D) primary RGCs were transfected with siRNAs against the various MAP kinases alone or in combination and survival was measured; (E) RGCs transfected with siRNAs against both MAP3K12/DLK and MAP3K13 were followed over time with calcein AM staining; and (F) RGCs were transfected with 10 nM siRNA against MAP3K12/DLK and MAP3K13 alone or in combination and then plated in 0, 12, 37, 111, 333, or 1000 nM sunitinib (left) or VX680 (right). Survival at 72 hours is shown;

FIGS. 4A and 4B show the upregulation of MAP3K12/DLK in response to retinal ganglion cell injury: (A) MAP3K12/DLK protein (top) and mRNA (bottom) were measured by immunoblotting and quantitative RT-PCR, respectively. GAPDH was used as loading control for both; (B) C57Bl/6 mice were subjected to unilateral optic nerve crush, the mice were sacrificed and the retinas were cryosectioned and stained for DAPI (top) or MAP3K12/DLK (bottom). Shown is a representative section demonstrating injury-induced upregulation of MAP3K12/DLK;

FIG. 5 shows retinal ganglion cell survival after the cells were transfected with MAP3K12/DLK siRNA;

FIG. 6A-6F demonstrate identification of MAP3K12/DLK as a mediator of cell death in RGCs: (A) RGCs were transfected at the time of immunopanning with a fluorescently-labeled siRNA (siGLO-Red, Dharmacon) in the presence or absence of the magnetic nanoparticle, NeuroMag. After 24 hours, RGCs were imaged for viability (calcein-AM staining) and nuclear accumulation of siRNA; (B) Histogram showing the normalized survival for control (black bars), kinome library (light bars), MAP3K12/DLK (solid arrows) and MKK7 (dashed arrows) siRNAs. Oligonucleotides conferring survival more than 3 SD from the nontargeting siRNAs (dashed line) were considered neuroprotective (106 siRNA, 5.4%); (C) RGCs were transfected with MAP3K12/DLK or a nontargeting control (NT) siRNA. mRNA (left) and protein (right) levels were quantified at 24 hours using RT-PCR and immunoblotting, respectively; (D) Survival of immunopanned RGCs transfected with nontargeting (dashed) or MAP3K12/DLK siRNA (solid); (E) Primary RGCs were transfected with MAP3K12/DLK or nontargeting control (NT) siRNA. After the indicated period of time (prior to cell death), cells were fixed and stained for Brn3 expression; and (F) Patch-clamp recordings from RGCs maintained with MAP3K12/DLK siRNA in response to depolarizing current;

FIG. 7 shows efficient transfection of primary RGCs. RGCs were reverse transfected with increasing doses of GAPDH or control small interfering RNA oligonucleotide in the presence of a fixed amount of NeuroMag and immunoblotted for GAPDH protein 24 h later;

FIGS. 8A-8B show secondary screening that confirmed the neuroprotective activity of dual leucine zipper kinase and MKK7 small interfering RNA oligonucleotides (siRNAs): (A) RGCs were immunopanned and transfected with an independent set of siRNAs not used in the initial screen. Candidate genes were considered confirmed if 75% of the secondary screening siRNA increased survival more than three SDs above the control siRNAs (dashed line); (B) RGCs were isolated from wild-type or Dlk$^{fl/fl}$ mice and immediately transduced with adeno-GFP or adeno-Cre. After 72 h, RGCs were imaged for viability by calcein-AM staining;

FIGS. 9A-9E show genetic deletion of MAP3K12/DLK protects RGCs from axonal injury-induced cell death in vivo: (A) Dlk+/+ mice were intravitreally injected with AAV2-Cre. Seven days after infection, retinal flatmounts were stained for βIII tubulin and Cre; (B) Three-month-old Dlk+/+ or Dlkfl/fl mice were intravitreally injected with AAV2-Cre. Seven days later, eyes were subjected to optic nerve crush. 4 days after injury, retinal flatmounts were prepared and stained for MAP3K12/DLK; (C) Survival of RGCs 10 days after optic nerve crush in Dlkfl/fl mice (n=7), Dlkfl/fl mice injected with AAV2-Cre (n=8) or Dlk+/+ mice injected with AAV2-Cre (n=9), normalized to uninjured controlmice (n=6). Representative images shown to the right. Immunofluorescent staining of optic nerves (D) and retinas (E) 24 hours after nerve crush in the mice described in (C). *$p<0.05$, #$p<0.005$; Error bars show standard deviation; and FIGS. 10A-10C show MAP3K12/DLK protein is upregulated in RGCs in response to injury: (A) Levels of MAP3K12/DLK protein (top) and mRNA (bottom), normalized to GAPDH, after various times in culture; (B) MAP3K12/DLK immunofluorescence of retinal sections 72 hours after optic nerve transection in rats; and (C) Survival, measured by CellTiter-Glo (CTG) luminescence, of immunopanned RGCs 48 hours after transduction with adenovirus expressing wildtype (WT) or kinase-dead (KD) MAP3K12/DLK. Western blot showing the upregulation of MAP3K12/DLK protein and corresponding response of the JNK pathway. *$p<0.05$; Error bars show standard deviation.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The following abbreviations are used throughout the specification and claims:
MAPK=mitogen-activated protein kinase spkl;
DLK=dual leucine zipper kinase;
LZK=leucine zipper-bearing kinase;
MAPKK=MAP2K, MAPK kinase;
MAPKKK=MAP3K, MAPKK kinase;
MKK=mitogen-activated protein kinase;
LYN=tyrosine-protein kinase encoded by the LYN gene;
PLK=polo-like kinase;
PFKP=phosphofructokinase, platelet;
MARK=microtubule affinity-regulating kinase;
TAOK=TAO kinase or serine/threonine protein kinase;
IKBKB=inhibitor of nuclear factor kappa-B kinase subunit beta;
BRSK=BR serine/threonine protein kinase;
PBK=lymphokine activated killer T cell originated protein kinase;
PRKCH=protein kinase C eta type;
TESK1=dual specificity testis-specific protein kinase 1;
Csnk1e=casein kinase 1 isoform epsilon;
Oxsr1=serine/threonine-protein kinase OSR1;
Tgfbr2=transforming growth factor, beta receptor II;
PFTK=transketolase;
ERN2=Serine/threonine-protein kinase/endoribonuclease IRE2;
ERN1=Serine/threonine-protein kinase/endoribonuclease IRE1;
AK2=adenylate kinase;
HSPB8=heat shock protein beta-8;
FRAP1=serine/threonine-protein kinase mTOR;
DGUOK=deoxyguanosine kinase, mitochondrial isoform b;
STK32B=serine/threonine-protein kinase 32B;
PIK3C2G=phosphatidylinositol-4-phosphate 3-kinase C2 domain-containing subunit gamma;
DYRK1A=dual specificity tyrosine-phosphorylation-regulated kinase 1A;
BCR=breakpoint cluster region;
PNCK=calcium/calmodulin-dependent protein kinase type 1B or pregnancy upregulated non-ubiquitously expressed CaM kinase;
EIF2AK1=Eukaryotic translation initiation factor 2-alpha kinase 1;
PKD2L1=Polycystic kidney disease 2-like 1 protein;
TLK2=serine/threonine-protein kinase tousled-like 2; and
MLK=mixed-lineage kinase.

I. Compounds, Compositions, and Methods for Treating Neurodegenerative Disorders Glaucoma, retinal degeneration (RD), and dAMD are a major cause of visual loss and blindness in America and throughout the world. One approach for treating glaucoma and other optic nerve diseases, as well as other neurodegenerative diseases, disorders, or conditions is through neuroprotective agents that promote the survival of neurons or a portion thereof (e.g., the neuron cell body, an axon, and/or a dendrite).

It previously has been shown that protein kinase inhibitors identified through a high content screen of libraries of small molecule compounds can promote the survival and/or neurite outgrowth of retinal ganglion cells (RGCs), photoreceptor, and RPE cells. They are active both in vitro and in vivo in animal models of optic nerve injury, and also in a rat photoreceptor degeneration model. See, for example, International PCT Patent Application Publication Nos., WO2010/017541, to Zack et al., published Feb. 11, 2010, and WO2011/119777 to Zack et al., published Sep. 29, 2011, each of which is incorporated by reference in their entirety.

RGCs are cells in the retina that die in glaucoma and whose loss leads to vision loss. Accordingly, based on the activity of the presently disclosed compounds on RGCs, the presently disclosed compounds can be used for treating glaucoma and/or other optic nerve diseases. Further, based on their activity on other neurons, e.g., photoreceptors and hippocampal cell cultures, the presently disclosed compounds can be used to treat other neurodegenerative diseases in which there is a decreased function and/or loss of neurons. In addition, based on their activity on RPE cells, as well as photoreceptor cells, the presently disclosed compounds can be used to treat dAMD.

A. Drug Targets and Pathways

In some embodiments, the presently disclosed subject matter identifies drug targets and pathways for treating retinal and other neurodegeneration: One approach to treating glaucoma, other optic nerve diseases, retinal degeneration, dAMD, as well as other neurodegeneration, is to develop "neuroprotective" agents that promote the survival of neurons. In some embodiments, the presently disclosed subject matter provides a screen assay, using RGC neurons damaged in glaucoma to identify novel drug targets. In further embodiments, the presently disclosed screening assay has been used to survey a portion of the mouse genome and, in doing so, has led to the identification of several novel targets that are involved in neuronal cell death (such that the cells survive when the targets are inhibited). One of these targets is only expressed following axonal damage and may represent a biomarker of neuronal injury in glaucoma and other neurodegeneration.

Accordingly, the presently disclosed subject matter includes: (a) design of a method to transfect retinal ganglion cell and screen for new neuroprotective drug targets; (b) identification of a novel neuroprotective drug target; (c) identification of a novel biomarker of neuronal injury (all current diagnostic tests for glaucoma measure anatomic and functional changes from retinal ganglion cell death); and (d) identification of the relevant target of neuroprotective protein kinase inhibitors.

Particular features of the presently disclosed subject matter include: (a) a high-throughput genetic screen (and the transfection method) to identify genes involved in the death and survival of primary neurons; (b) genes identified as being involved in retinal ganglion cell death. Further, for the first time, the targeting of those genes by siRNA and small molecule inhibitors to treat retinal ganglion cell degeneration (like glaucoma) is described; and (c) identification of a gene that is selectively expressed in injured neurons.

B. Methods of Treatment

In some embodiments, the presently disclosed subject matter identifies molecular pathways involved in the mechanism by which retinal ganglion cells (RGCs) die in glaucoma, and the same or similar mechanisms also may represent the pathways by which photoreceptor cells die in the retinal degeneration (RD) and in dAMD, which also includes death of RPE cells. The pathways were identified by a whole kinome screen in which short interfering or silencing RNAs (siRNAs) were used to knockdown separately each of the kinases in cultured RGCs, and the effect of such knockdown on RGC survival was assayed.

In other aspects, the presently disclosed subject matter provides a method for treating or preventing a neurodegenerative disease, disorder, or condition in a subject in need thereof, the method comprising administering to the subject a therapeutically effective amount of a compound, such as a small molecule protein kinase inhibitor, or a pharmaceutically acceptable salt thereof, that inhibits one of the specific identified pathways or kinases, thereby treating or preventing the neurodegenerative disease, disorder, or condition; or use of a genomic reagent, such as a siRNA, or a modified siRNA, that directly or indirectly modifies the expression of the identified drug target, its biochemical activity, or otherwise modifies the activity of the identified pathway. In particular embodiments, the neurodegenerative disease, disorder, or condition is an ocular-related neurodegeneration, such as glaucoma, RD, or dAMD.

In one embodiment, the presently disclosed subject matter describes a method for inhibiting or preventing retinal ganglion cell injury or death, the method comprising contacting the retinal ganglion cell with a small molecule that modulates protein kinase expression or activity. Examples of the protein kinase include MAP3K12, MAP3K13, MAP3K14, MAP2K7, MAP2K4, LYN, PLK3, PFKP MARK3, MARK2, TAOK1, IKBKB, BRSK2, PBK, PRKCH, TESK1, Csnk1e, Oxsr1, Tgfbr2, Mapk10, PFTK1, ERN2, AK2, HSPB8, FRAP1, DGUOK, ERN1, STK32B, PIK3C2G, BCR, DYRK1A, DYRK1B, PNCK, EIF2AK1, PKD2L1, NRK, Endothelin Receptor Type B, and TLK2. The modulation of protein kinase activity or expression may be an inhibition or increase in protein kinase activity or expression. In one embodiment, the small molecule is a short interfering or silencing RNA (siRNA). In a further embodiment, the siRNA targets are selected from the group consisting of MAP3K12, MAP3K13, MAP2K4, and MAP2K7.

The contacting of the cell with a small molecule can be performed ex vivo or in vivo. It may further comprise grafting or implanting the cell into a subject after contacting the cell with a small molecule. The grafting or implanting the cell into a subject can occur in a pharmaceutically acceptable carrier. The inhibiting or preventing retinal ganglion cell injury or death may treat or prevent an ocular neurodegenerative disease, such as glaucoma, retinal degeneration, or age-related macular degeneration. The modulation of protein kinase expression or activity may be an inhibition of expression or activity or an increase in expression or activity. The small molecule may be a short interfering RNA (siRNA), such as a siRNA targeting MAP3K12, MAP3K13, MAP2K4, or MAP2K7. Thus, the presently disclosed methods may involve administering a small molecule, such as a siRNA, to a subject. Administering to a subject may occur via a pharmaceutically acceptable carrier.

In some embodiments, the ocular neurodegenerative disease is selected from the group consisting of glaucoma, retinal degeneration, and age-related macular degeneration.

In some embodiments, the presently disclosed subject matter provides a compound that promotes neuroprotection by inhibiting any of the molecules, activities, or pathways provided herein in Table 1. A specific example is the use of a small molecule to inhibit the protein kinase MAP3K12 (also known as DLK) and other members of the mixed-lineage kinase family to achieve neuroprotective treatment of glaucoma, RD, dAMD, and other forms of ocular neurodegeneration, as well as forms of CNS neurodegeneration. A more specific example is the use of CEP-1347, CEP-11004, and other MLK inhibitors to promote retinal neuronal health and survival.

TABLE 1

Drug/Pathway Targets

| | |
|---|---|
| MAP3K12/DLK | (GenBank Accession No. NM_006301) |
| MAP3K13 | (GenBank Accession No. NM_004721) |
| MAP3K14 (isoform 1) | (RefSeq Accession No. NP_001180440) |
| MAP2K7 | (GenBank Accession No. AAH38295) |
| MAP2K4 | (GenBank Accession No. CAG38801) |
| LYN | (RefSeq Accession No. NP_002341) |
| PLK3 | (RefSeq Accession No. NP_004064) |
| PFKP | (GenBank Accession No. AAH02536) |
| MARK3 (isoform a) | (RefSeq Accession No. NP_001122390) |
| MARK2 (isoform a) | (RefSeq Accession No. NP_059672) |
| TAOK1 | (GenBank Accession No. AA144068) |
| IKBKB (isoform 1) | (RefSeq Accession No. NP_001547) |
| BRSK2 (isoform 1) | (RefSeq Accession No. NP_001243558) |
| PBK | (RefSeq Accession No. NP_060962) |
| PRKCH | (RefSeq Accession No. NP_006246) |
| TESK1 | (RefSeq Accession No. NP_006276) |
| Csnk1e | (RefSeq Accession No. NP_689407) |
| Oxsr1 | (RefSeq Accession No. NP_005100) |
| Tgfbr2 | (GenBank Accession No. ABG65632) |
| Mapk10 | (GenBank Accession No. AAH51731) |
| PFTK1 | (GenBank Accession No. AA136477) |
| ERN2 | (RefSeq Accession No. NP_150296) |
| AK2 (mitochondrial isoform a) | (RefSeq Accession No. NP_001616) |
| HSPB8 | (RefSeq Accession No. NP_055180) |
| FRAP1 | (RefSeq Accession No. NP_004949) |
| DGUOK (mitochondrial isoform b) | (RefSeq Accession No. NP_550440) |
| ERN1 | (RefSeq Accession No. NP_001424) |
| STK32B | (RefSeq Accession No. NP_060871) |
| PIK3C2G | (RefSeq Accession No. NP_004561) |
| BCR (isoform 1) | (RefSeq Accession No. NP_004318) |
| DYRK1A (isoform 1) | (RefSeq Accession No. NP_001387) |
| PNCK | (GenBank Accession No. AAH64422) |
| EIF2AK1 (isoform a) | (RefSeq Accession No. NP_055228) |
| PKD2L1 (isoform 1) | (RefSeq Accession No. NP_057196) |
| TLK2 (isoform A) | (RefSeq Accession No. NP_006843) |

Accordingly, in some embodiments, the MLK inhibitor is a compound of Formula (I):

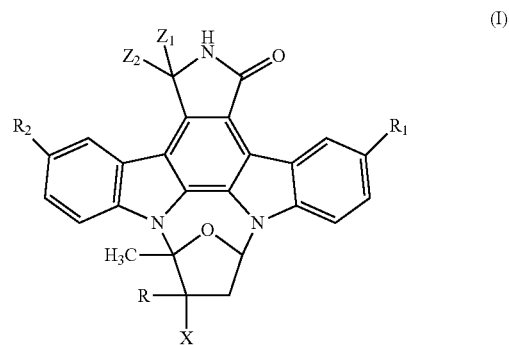

wherein:
$R_1$ is selected from the group consisting of H, halogen, alkyl, —OH, —NHCONHC$_6$H$_5$, CH$_2$SOC$_2$H$_5$, —NHCONHC$_2$H$_5$, —CH$_2$SC$_2$H$_5$, —CH$_2$SC$_2$H$_5$, —NHCONHC$_2$H$_5$, —R$_3$R$_4$, wherein R$_3$ and R$_4$ are each H or alkyl, —CH$_2$OCONHC$_2$H$_5$, —NHCO$_2$CH$_3$, —CH$_2$OC$_2$H$_5$, —CH$_2$N(CH$_3$)$_2$, —CH$_2$SO$_2$C$_2$H$_5$, —CH$_2$S—O$_5$H$_4$N, —CH$_2$SC$_2$H$_5$, —CH_NNH—O$_5$N$_2$H$_5$, —CH$_2$S—C$_4$N$_2$H$_3$, —CH$_2$S(O)—C$_4$N$_2$H$_3$, —CH$_2$S(O)C$_5$H$_4$, —CH$_2$SC$_2$H$_5$, O-n-propyl, —CH$_2$SCH$_2$CH$_2$N(CH$_3$)$_2$, —CH$_2$S-benzimidazole, —CH$_2$SCH$_2$-furan, —CH=N-pyrrolidine, —CH=NNH-pyridine, —CH$_2$S(CH$_2$)$_2$NH$_2$, —CH$_2$-1,2,4-triazole, —CH=NNH—C(=NH)NH$_2$, —CH=N-1,2,4-triazole, —CH=N-mopholine, —CHN—N(CH$_3$)$_2$, —CH=N-1-methylpiperazine, —CHCH$_2$S(CH$_2$)$_2$NH-n-C$_4$H$_9$, and —CH$_2$S—(CH$_2$)$_2$N(CH$_3$)$_2$;

R$_2$ is selected from the group consisting of H, halogen, —NHCONHC$_2$H$_5$, —CH$_2$SC$_2$H$_5$, —CH$_2$OH, —NH$_2$, —CH$_2$S(CH$_2$)$_2$—N(CH$_3$)$_2$;

X is selected from the group consisting of H, —CH$_2$N$_3$, —CO$_2$CH$_3$, —CH$_2$OH, —CONHC$_2$H$_5$, —CH=NNH—C$_3$N$_2$H$_5$, —CH$_2$NH-Gly, —CON(CH$_3$)$_2$, —CH$_2$NHCO$_2$, —CONH$_2$, —CONHCC$_3$H$_7$, —CH$_2$NH-Ser, —CH$_2$SOCH$_3$, —CH=NOH, —C—O-morpholine, —CH$_2$NH-Pro, —CH=NNHC(=NH)NH$_2$, —CONH(CH$_2$)OH, —CO$_2$CH$_3$, —CH=NNHCONH$_2$, —CH$_2$OCOCH$_3$, —CONHC$_6$H$_5$, —CH$_2$SO-pyridine, —CH$_2$NHCO$_2$C$_6$H$_5$, —CH$_2$OH, —CONHC$_6$H$_5$, —CONHCH$_2$CH$_2$OH, CH$_2$NHCO$_2$CH$_3$, —CONH$_2$, —CH$_2$SC$_6$H$_5$, —CH$_2$S-pyridine, —CH$_2$SOC$_6$H$_5$, —CO$_2$-n-hexyl, —CH$_2$NH$_2$, and —CONHCH$_3$;

R is selected from the group consisting of —OH and -methoxyl;

Z$_1$ and Z$_2$ are selected from the group consisting H and O; and pharmaceutically acceptable salts thereof.

In particular embodiments, the MLK inhibitor is CEP-1347, which has the following structure:

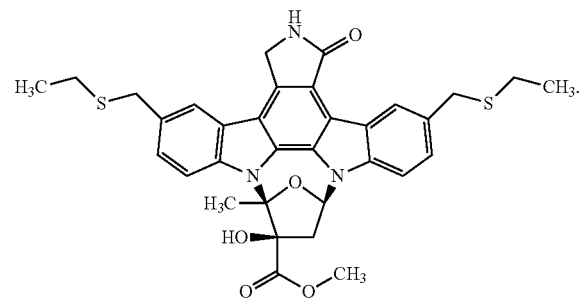 [SMILES: CCSCc1ccc2c(c1)c1c3c(c4c5cc(CSCC)ccc5n5c4c1n2[C@H]1C[C@](O)(C(=O)OC)[C@]5(C)O1)CNC3=O]

In other embodiments, the MLK inhibitor is CEP-11004, which has the following structure:

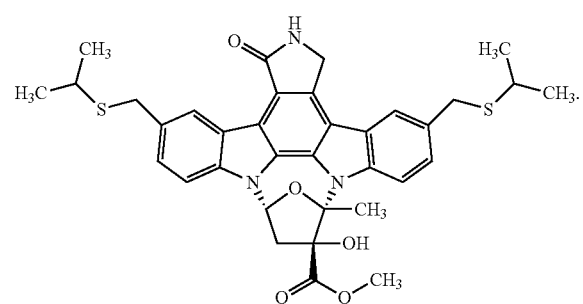 [SMILES: COC(=O)[C@@]1(O)C[C@H]2O[C@]1(C)n1c3ccc(CSC(C)C)cc3c3c4c(c5c6cc(CSC(C)C)ccc6n2c5c31)C(=O)NC4]

In particular embodiments, the protein kinase inhibitor is a compound disclosed in U.S. Pat. No. 5,621,100 or International PCT Patent Application Publication No. WO9402488, each of which is incorporated herein by reference in its entirety.

In other embodiments, the presently disclosed subject matter provides a compound that promotes neuroprotection by stimulating any of the molecules, activities, or pathways provided herein in Table 1.

In further embodiments, the presently disclosed subject matter provides a siRNA, modified siRNA, shRNA, modified shRNA, or other molecule or method that promotes neuroprotection by decreasing expression or activity of any of the molecules or pathways provided herein in Table 1.

In yet further embodiments, the presently disclosed subject matter provides a siRNA, modified siRNA, shRNA, modified shRNA, or other molecule or method that promotes neuroprotection by increasing expression or activity of any of the molecules or pathways provided herein in Table 1.

A variety of means are available for altering a gene to effect expression. In a particular embodiment the expression of a gene encoding a protein kinase is reduced by contacting the gene, or an mRNA transcribed from the gene, with a compound comprising a polynucleotide selected from the group consisting of an antisense oligonucleotide, a ribozyme, a small interfering RNA (siRNA), and a short hairpin RNA (shRNA). In a particularly preferred embodiment the compound comprises a nucleotide sequence complementary to a nucleotide sequence comprising the polynucleotide sequence of MAP3K12, MAP3K13, MAP2K4, or MAP2K7.

The term "polynucleotide" means a polynucleic acid, in single or double stranded form, and in the sense or antisense orientation, complementary polynucleic acids that hybridize to a particular polynucleic acid under stringent conditions, and polynucleotides that are homologous in at least about 60 percent of its base pairs, and more preferably 70 percent of its base pairs are in common, most preferably 90 percent, and in a special embodiment 100 percent of its base pairs. The polynucleotides include polyribonucleic acids, polydeoxyribonucleic acids, and synthetic analogues thereof. The polynucleotides are described by sequences that vary in length, that range from about 10 to about 5000 bases, preferably about 100 to about 4000 bases, more preferably about 250 to about 2500 bases. A preferred polynucleotide embodiment comprises from about 10 to about 30 bases in length. A particular embodiment of polynucleotide is the polyribonucleotide of from about 10 to about 22 nucleotides, more commonly described as small interfering RNAs (siRNAs). Another special embodiment are nucleic acids with modified backcartilages such as peptide nucleic acid (PNA), polysiloxane, and 2'-O-(2-methoxy)ethylphosphorothioate, or including non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection.

The term "antisense nucleic acid" refers to an oligonucleotide that has a nucleotide sequence that interacts through base pairing with a specific complementary nucleic acid sequence involved in the expression of the target such that the expression of the gene is reduced. Preferably, the specific nucleic acid sequence involved in the expression of the gene is a genomic DNA molecule or mRNA molecule that encodes (a part of) the gene. This genomic DNA molecule can comprise regulatory regions of the gene, or the coding sequence for the mature gene.

The term "complementary to a nucleotide sequence" in the context of antisense oligonucleotides and methods should be understood as sufficiently complementary to such a sequence as to allow hybridization to that sequence in a cell, i.e., under physiological conditions.

The term "hybridization" means any process by which a strand of nucleic acid binds with a complementary strand through base pairing. The term "hybridization complex" refers to a complex formed between two nucleic acid sequences by virtue of the formation of hydrogen bonds between complementary bases. A hybridization complex may be formed in solution or formed between one nucleic acid sequence present in solution and another nucleic acid sequence immobilized on a solid support (e.g., paper, membranes, filters, chips, pins or glass slides, or any other appropriate protein kinase to which cells or their nucleic acids have been fixed). The term "stringent conditions" refers to conditions that permit hybridization between polynucleotides and the claimed polynucleotides. Stringent conditions can be defined by salt concentration, the concentration of organic solvent, e.g., formamide, temperature, and other conditions well known in the art. In particular, reducing the concentration of salt, increasing the concentration of formamide, or raising the hybridization temperature can increase stringency.

The down regulation of gene expression using antisense nucleic acids can be achieved at the translational or transcriptional level using an expression-inhibitory agent. Antisense nucleic acids of the invention are preferably nucleic acid fragments capable of specifically hybridizing with all or part of a nucleic acid encoding a protein kinase or the corresponding messenger gene or mRNA. In addition, antisense nucleic acids may be designed which decrease expression of the nucleic acid sequence capable of encoding a protein kinase by inhibiting splicing of its primary transcript. Any length of antisense sequence is suitable for practice of the invention so long as it is capable of down-regulating or blocking expression of a nucleic acid coding for a protein kinase. Preferably, the antisense sequence is at least about 17 nucleotides in length. The preparation and use of antisense nucleic acids, DNA encoding antisense RNAs and the use of oligo and genetic antisense is known in the art.

The term "expression inhibitory agent" means a polynucleotide designed to interfere selectively with the transcription, translation and/or expression of a specific polypeptide or protein normally expressed within a cell. More particularly, "expression inhibitory agent" comprises a DNA or RNA molecule that contains a nucleotide sequence identical to or complementary to at least about 17 sequential nucleotides within the polyribonucleotide sequence coding for a specific polypeptide or protein. Exemplary expression inhibitory molecules include ribozymes, double stranded siRNA molecules, self-complementary single-stranded siRNA molecules, genetic antisense constructs, and synthetic RNA antisense molecules with modified stabilized backbones.

One embodiment of expression-inhibitory agent is a nucleic acid that is antisense to a nucleotide sequence comprising the polynucleotide sequence of MAP3K12, MAP3K13, MAP2K4, or MAP2K7. For example, an antisense nucleic acid (e.g. DNA) may be introduced into cells in vitro, or administered to a subject in vivo, as gene therapy to inhibit cellular expression of nucleotide sequence comprising the polynucleotide sequence of MAP3K12, MAP3K13, MAP2K4, or MAP2K7. Antisense oligonucleotides preferably comprise a sequence containing from about 17 to about 100 nucleotides and more preferably the antisense oligonucleotides comprise from about 18 to about 30 nucleotides. Antisense nucleic acids may be prepared from about 10 to about 30 contiguous nucleotides complementary to a nucleotide sequence comprising the polynucleotide sequence of MAP3K12, MAP3K13, MAP2K4, or MAP2K7.

The antisense nucleic acids are preferably oligonucleotides and may consist entirely of deoxyribo-nucleotides, modified deoxyribonucleotides, or some combination of both. The antisense nucleic acids can be synthetic oligonucleotides. The oligonucleotides may be chemically modified, if desired, to improve stability and/or selectivity. Since oligonucleotides are susceptible to degradation by intracellular nucleases, the modifications can include, for example, the use of a sulfur group to replace the free oxygen of the phosphodiester bond. This modification is called a phosphorothioate linkage. Phosphorothioate antisense oligonucleotides are water soluble, polyanionic, and resistant to endogenous nucleases. In addition, when a phosphorothioate antisense oligonucleotide hybridizes to its mRNA target, the $RN_2O_2$-315NA duplex activates the endogenous enzyme ribonuclease (RNase) H, which cleaves the mRNA component of the hybrid molecule.

In addition, antisense oligonucleotides with phosphoramidite and polyamide (peptide) linkages can be synthesized. These molecules should be very resistant to nuclease degradation. Furthermore, chemical groups can be added to the 2' carbon of the sugar moiety and the 5 carbon (C-5) of pyrimidines to enhance stability and facilitate the binding of the antisense oligonucleotide to its target site. Modifications may include 2'-deoxy, O-pentoxy, O-propoxy, O-methoxy, fluoro, methoxyethoxy phosphorothioates, modified bases, as well as other modifications known to those of skill in the art.

Another type of expression-inhibitory agent that reduces the levels of mRNA is the ribozyme. Ribozymes are catalytic RNA molecules (RNA enzymes) that have separate catalytic and substrate binding domains. The substrate binding sequence combines by nucleotide complementarity and, possibly, non-hydrogen bond interactions with its mRNA sequence. The catalytic portion cleaves the mRNA at a specific site. The substrate domain of a ribozyme can be engineered to direct it to a specified mRNA sequence. The ribozyme recognizes and then binds protein kinase mRNA through complementary base pairing. Once it is bound to the correct protein kinase mRNA site, the ribozyme acts enzymatically to cut the protein kinase mRNA. Cleavage of the mRNA by a ribozyme destroys its ability to direct synthesis of the corresponding polypeptide. Once the ribozyme has cleaved its protein kinase mRNA sequence, it is released and can repeatedly bind and cleave at other mRNAs. Ribozyme forms include a hammerhead motif, a hairpin motif, a hepatitis delta virus, group I intron or RNaseP RNA (in association with an RNA guide sequence) motif or Neurospora VS RNA motif Ribozymes possessing a hammerhead or hairpin structure are readily prepared since these catalytic RNA molecules can be expressed within cells from eukaryotic promoters (Chen et al. Nucleic Acids Res. 20:4581-9, 1985). A ribozyme of the presently disclosed subject matter can be expressed in eukaryotic cells from the appropriate DNA vector.

If desired, the activity of the ribozyme may be augmented by its release from the primary transcript by a second ribozyme (Ventura et al. Nucleic Acids Res. 21:3249-55, 1983).

The term "vectors" relates to plasmids as well as to viral vectors, such as recombinant viruses, or the nucleic acid encoding the recombinant virus.

Ribozymes may be chemically synthesized by combining an oligodeoxyribonucleotide with a ribozyme catalytic domain (20 nucleotides) flanked by sequences that hybridize to the protein kinase mRNA after transcription. The oligodeoxyribonucleotide is amplified by using the substrate binding sequences as primers. The amplification product is cloned into a eukaryotic expression vector.

Ribozymes are expressed from transcription units inserted into DNA, RNA, or viral vectors. Transcription of the ribozyme sequences are driven from a promoter for eukaryotic RNA polymerase I (pol (I), RNA polymerase II (pol II), or RNA polymerase III (pol III). Transcripts from pol II or pol III promoters will be expressed at high levels in all cells; the levels of a given pol II promoter in a given cell type will depend on nearby gene regulatory sequences. Prokaryotic RNA polymerase promoters are also used, providing that the prokaryotic RNA polymerase enzyme is expressed in the appropriate cells (Gao and Huang, Nucleic Acids Res. 21:2867-72, 1993). It has been demonstrated that ribozymes expressed from these promoters can function in mammalian cells (Kashani-Sabet et al., Antisense Res. Dev. 2:3-15, 1992).

A particularly preferred inhibitory agent is a small interfering RNA (siRNA). siRNA, preferably short hairpin RNA (shRNA), mediate the post-transcriptional process of gene silencing by double stranded RNA (dsRNA) that is homologous in sequence to the silenced RNA. siRNA according to the presently disclosed subject matter comprises a sense strand of 17-25 nucleotides complementary or homologous to a contiguous 17-25 nucleotide sequence of the polynucleotide sequence of MAP3K12 (GenBank Accession No, NM 006301) or MAP3K13 (Genbank Accession Number NM 004721), and an antisense strand of 17-23 nucleotides complementary to the sense strand. The most preferred siRNA comprises sense and anti-sense strands that are 100 percent complementary to each other and the protein kinase polynucleotide sequence. Preferably the siRNA further comprises a loop region linking the sense and the antisense strand. A self-complementing single stranded siRNA molecule polynucleotide according to the presently disclosed subject matter comprises a sense portion and an antisense portion connected by a loop region linker. The loop can be any length but is preferably 4-30 nucleotides long. Self-complementary single stranded siRNAs form hairpin loops and are more stable than ordinary dsRNA. In addition, they are more easily produced from vectors.

Analogous to antisense RNA, the siRNA can be modified to confirm resistance to nucleolytic degradation, or to enhance activity, or to enhance cellular distribution, or to enhance cellular uptake, such modifications may consist of modified internucleoside linkages, modified nucleic acid bases, modified sugars and/or chemical linkage the siRNA to one or more moieties or conjugates.

The presently disclosed subject matter also relates to compositions and methods comprising a DNA expression vector capable of expressing a polynucleotide capable of increasing resistance to cell damage and is described hereinabove as an expression inhibition agent.

In another embodiment, the presently disclosed compositions and methods relate to the down-regulation or blocking of the expression of a protein kinase by the induced expression of a polynucleotide encoding an intracellular binding protein that is capable of selectively interacting with the protein kinase polypeptide. An intracellular binding protein includes any protein capable of selectively interacting, or binding, with the polypeptide in the cell in which it is expressed and neutralizing the function of the polypeptide. Preferably, the intracellular binding protein is a neutralizing antibody or a fragment of a neutralizing antibody having binding affinity to an epitope of the protein kinase. More preferably, the intracellular binding protein is a single chain antibody.

The term "binding affinity" is a property that describes how strongly two or more compounds associate with each other in a non-covalent relationship. Binding affinities can be characterized qualitatively, (such as "strong", "weak", "high", or "low") or quantitatively (such as measuring the KO.

In a particular embodiment, the composition comprises an expression-inhibiting agent selected from the group consisting of antisense RNA, antisense oligodeoxynucleotide (ODN), and a small interfering RNA (siRNA) that is sufficiently homologous to a portion of the polynucleotide encoding a target protein kinase such that the siRNA interferes with the translation of the protein kinase polyribonucleotide to the protein kinase polypeptide.

The polynucleotide expressing the expression-inhibiting agent is preferably included within a vector. The polynucleic acid is operably linked to signals enabling expression of the nucleic acid sequence and is introduced into a cell utilizing, preferably, recombinant vector constructs, which will express the antisense nucleic acid once the vector is introduced into the cell. A variety of viral-based systems are available, including adenoviral, retroviral, adeno-associated viral, lentiviral, herpes simplex viral or a sendaviral vector systems, and all may be used to introduce and express polynucleotide sequence for the expression-inhibiting agents in protein kinase-expressing cells.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e.g. enhancers) in an expression vector. Transcriptional and translational control sequences are DNA expression regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Promoters that may be used in the expression vectors of the presently disclosed subject matter include both constitutive promoters and regulated (inducible) promoters.

Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

In a particular embodiment, the viral element is derived from an adenovirus. Other embodiments of the presently disclosed subject matter use retroviral vector systems which can be constructed from different types of retrovirus, such as, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Lentiviral vector systems may also be used in the practice of the presently disclosed subject matter. In other embodiments of the presently disclosed subject matter, adeno-associated viruses ("AAV") may be utilized.

Preferably, the viral vectors used in the methods of the presently disclosed subject matter are replication defective. Such replication defective vectors will usually pack at least one region that is necessary for the replication of the virus in the infected cell. These regions can either be eliminated (in whole or in part), or be rendered non-functional by any technique known to a person skilled in the art. These techniques include the total removal, substitution, partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome, which are necessary for encapsidating, the viral particles.

In the vector construction, the polynucleotide agents of the presently disclosed subject matter may be linked to one or more regulatory regions. Selection of the appropriate regulatory region or regions is a routine matter, within the level of ordinary skill in the art. Regulatory regions include promoters, and may include enhancers, suppressors, and the like.

Additional vector systems include the non-viral systems that facilitate introduction of polynucleotide agents into a patient. For example, a DNA vector encoding a desired sequence can be introduced in vivo by lipofection. Synthetic cationic lipids designed to limit the difficulties encountered with liposome-mediated transfection can be used to prepare liposomes for in vivo transfection of a gene encoding a marker (Feigner et. al., Proc. Natl. Acad. Sci. USA 84:7413-7, 1987); see Mackey et al., Proc. Natl. Acad. Sci. USA 85:8027-31, 1988; Ulmer et al., Science 259:1745-8, 1993). The use of cationic lipids may promote encapsulation of negatively charged nucleic acids, and also promote fusion with negatively charged cell membranes (Feigner and Ringold, Nature 337:387-8, 1989). Particularly useful lipid compounds and compositions for transfer of nucleic acids are described in International PCT Patent Publications WO 95/18863 and WO 96/17823, and in U.S. Pat. No. 5,459,127. The use of lipofection to introduce exogenous genes into the specific organs in vivo has certain practical advantages and directing transfection to particular cell types would be particularly advantageous in a tissue with cellular heterogeneity, for example, pancreas, liver, kidney, and the brain. Lipids may be chemically coupled to other molecules for the purpose of targeting. Targeted peptides, e.g., hormones or neurotransmitters, and proteins for example, antibodies, or non-peptide molecules could be coupled to liposomes chemically. Other molecules are also useful for facilitating transfection of a nucleic acid in vivo, for example, a cationic oligopeptide (e.g., International PCT Patent Publication WO 95/21931), peptides derived from DNA binding proteins (e.g., International PCT Patent Publication WO 96/25508), or a cationic polymer (e.g., International PCT Patent Publication WO 95/21931).

It is also possible to introduce a DNA vector in vivo as a naked DNA plasmid (see U.S. Pat. Nos. 5,693,622, 5,589,466 and 5,580,859). Naked DNA vectors for therapeutic purposes can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wilson et al., J. Biol. Chem. 267:963-7, 1992; Wu and Wu, J. Biol. Chem. 263:14621-4, 1988; Hartmut, et al. Canadian Patent Application No. 2,012,311, filed Mar. 15, 1990; Williams et al, Proc. Natl. Acad. Sci. USA 88:2726-30, 1991). Receptor-mediated DNA delivery approaches can also be used (Curiel, et al., Hum. Gene Ther. 3:147-54, 1992; Wu and Wu, J. Biol. Chem. 262:4429-32, 1987).

In particular embodiments, the neurodegenerative disease, disorder, or condition is an ocular-related neurodegeneration. In more particular embodiments, the ocular-related neurodegeneration is selected from the group consisting of glaucoma, lattice dystrophy, retinitis pigmentosa, age-related macular degeneration (AMD), photoreceptor degeneration associated with wet or dry AMD, other retinal degeneration, optic nerve drusen, optic neuropathy, and optic neuritis, such as optic neuritis resulting from multiple sclerosis.

In yet more particular embodiments, the glaucoma is selected from the group consisting of primary glaucoma, low-tension glaucoma, primary angle-closure glaucoma, acute angle-closure glaucoma, chronic angle-closure glaucoma, intermittent angle-closure glaucoma, chronic open-angle closure glaucoma, pigmentary glaucoma, exfoliation glaucoma, developmental glaucoma, secondary glaucoma, phacogenic glaucoma, glaucoma secondary to intraocular hemorrhage, traumatic glaucoma, neovascular glaucoma, drug-induced glaucoma, toxic glaucoma, and glaucoma associated with intraocular tumors, retinal detachments, severe chemical burns of the eye, and iris atrophy.

In other embodiments, the neurodegenerative disease, disorder, or condition is or is associated with a disease, disorder, or condition of the nervous system selected from the group consisting of amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, Alzheimer's disease, Huntington's disease, Parkinson's disease, Parkinson's-plus diseases, multiple system atrophy, progressive supranuclear palsy, corticobasal degeneration, dementia with Lewy bodies, frontotemporal dementia, demyelinating diseases, Guillain-Barre syndrome, multiple sclerosis, Charcot-Marie-Tooth disease, prion diseases, Creutzfeldt-Jakob disease, Gerstmann-Straussler-Scheinker syndrome (GSS), fatal familial insomnia (FFI), bovine spongiform encephalopathy (BSE), Pick's disease, epilepsy, AIDS demential complex, alcoholism, Alexander's disease, Alper's disease, ataxia telangiectasia, Batten disease, Canavan disease, Cockayne syndrome, diabetic neuropathy, frontotemporal lobar degeneration, HIV-associated dementia, Kennedy's disease, Krabbe's disease, neuroborreliosis, Machado-Joseph disease (Spinocerebellar ataxia type 3), wet or dry macular degeneration, Niemann Pick disease, Pelizaeus-Merzbacher Disease, photoreceptor degenerative diseases, Refsum's disease, Sandhoffs disease, Schilder's disease, subacute combined degeneration of spinal cord secondary to pernicious anemia, Spielmeyer-Vogt-Sjogren-Batten disease (also known as Batten disease), spinocerebellar ataxia (multiple types with varying characteristics), Steele-Richardson-Olszewski disease, and tabes dorsalis.

In yet other embodiments, the neurodegenerative disease, disorder, or condition comprises one or more conditions that are secondary to a disease, disorder, condition, or therapy having a primary effect outside of the nervous system selected from the group consisting of: peripheral neuropathy or neuralgia caused by diabetes, cancer, AIDS, hepatitis, kidney dysfunction, Colorado tick fever, diphtheria, HIV infection, leprosy, Lyme disease, polyarteritis nodosa, rheumatoid arthritis, sarcoidosis, Sjogren syndrome, syphilis, systemic lupus erythematosus, and amyloidosis.

In other embodiments, the neurodegenerative disease, disorder, or condition is associated with pain selected from the group consisting of chronic pain, fibromyalgia, spinal pain, carpel tunnel syndrome, pain from cancer, arthritis, sciatica, headaches, pain from surgery, muscle spasms, back pain, visceral pain, pain from injury, dental pain, neuralgia, such as neurogenic or neuropathic pain, nerve inflammation or damage, shingles, herniated disc, a torn ligament, and diabetes.

In further embodiments, the neurodegenerative disease, disorder, or condition is associated with one or more injuries to the nervous system. In particular embodiments, the one or more injuries to the nervous system is related to nerve damage caused by exposure to one or more agents selected from the group consisting of toxic compounds, heavy metals, industrial solvents, drugs, chemotherapeutic agents, dapsone, HIV medications, cholesterol lowering drugs, heart or blood pressure medications, and metronidazole.

In more particular embodiments, the one or more injuries to the nervous system is related to nerve damage caused by one or more conditions selected from the group consisting of burn, wound, surgery, accidents, ischemia, prolonged exposure to cold temperature, stroke, intracranial hemorrhage, and cerebral hemorrhage.

In yet other embodiments, the neurodegenerative disease, disorder, or condition comprises a psychiatric disorder. In particular embodiments, the psychiatric disorder is selected from the group consisting of schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders.

In some embodiments, the method promotes or stimulates neurite growth or regeneration from one or more neuronal cells.

In further embodiments, the method comprises treating one or more neuronal cells in preparation for a nerve transplantation procedure. In particular embodiments, the treating is before, during, or after the transplantation procedure.

In other embodiments, the method treats or prevents a neuronal cell loss in the subject. In yet other embodiments, the method prevents neuronal cell death in the subject. In some embodiments, the method prevents apoptosis of one or more neuronal axons in the subject.

In some embodiments, an additional therapeutic agent is administered to the subject. In particular embodiments, the additional therapeutic agent is selected from the group consisting of a beta-blocker, an alpha-agonist, a carbonic anhydrase inhibitor, a prostaglandin or a prostaglandin analog, a miotic or a cholinergic agent, an epinephrine compound, forskolin, and one or more additional neuroprotective compounds.

In some embodiments, the compound against the identified target, or pathway, or a pharmaceutically acceptable salt thereof, is administered to the subject by a method selected from the group consisting of oral, topical, parenteral, and systemic.

In other embodiments, the presently disclosed subject matter provides a method for treating or preventing a neurodegenerative disease, disorder, or condition in a subject in need thereof, the method comprising administering to the subject a therapeutically effective amount of a compound that modifies one of the described molecular targets of associated signaling pathway, or a pharmaceutically acceptable salt thereof, or a siRNA, shRNA, or other gene expression or kinase or pathway modifying agent, thereby treating or preventing the neurodegenerative disease, disorder, or condition.

As used herein, a "neuron or portion thereof" can consist of or be a portion of a neuron selected from the group consisting of a cerebellar granule neuron, a dorsal root ganglion neuron, a cortical neuron, a sympathetic neuron, and a hippocampal neuron. More particularly, the term "neuron" as used herein denotes nervous system cells that include a central cell body or soma, and two types of extensions or projections: dendrites, by which, in general, the majority of neuronal signals are conveyed to the cell body; and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column) Certain specific examples of neuron types that may be subject to treatment according to the presently disclosed subject matter include cerebellar granule neurons, dorsal root ganglion neurons, and cortical neurons. Further, as used herein, the term "neurite" means a projection from the cell body of a neuron including, e.g., an axon or a dendrite.

Without wishing to be bound to any one particular theory, it is believed that the presently disclosed targets and pathways can modulate: (i) the activity or expression of a target protein in the neuron or portion thereof; (ii) a process in the neuron or portion thereof; or (iii) a biological pathway associated with a neurodegenerative disease, disorder, or condition. In particular embodiments, the presently disclosed compounds inhibit one or more protein kinases involved in a biological pathway associated with a neurodegenerative disease, disorder, or condition. As used herein, the term "inhibit" or "inhibits" means to decrease, suppress, attenuate, diminish, arrest, or stabilize the development or progression of a disease, disorder, or condition, or the activity of a biological pathway, e.g., by at least 10%, 20%, 30%, 40%, 50%, 60%, 70%, 80%, 90%, 95%, 98%, 99%, or even 100% compared to an untreated control subject, cell, or biological pathway. By the term "decrease" is meant to inhibit, suppress, attenuate, diminish, arrest, or stabilize a symptom of a neurodegenerative disease, disorder, or condition. It will be appreciated that, although not precluded, treating a disease, disorder or condition does not require that the disease, disorder, condition or symptoms associated therewith be completely eliminated.

In some embodiments, the neuron or portion thereof can be present in a subject, such as a human subject. The subject can, for example, have or be at risk of developing a disease, disorder, or condition selected from the group consisting of (i) a disease, disorder, or condition of the nervous system; (ii) a condition of the nervous system that is secondary to a disease, disorder, or condition, or a therapy having a primary effect outside of the nervous system; (iii) an injury to the nervous system, such as, for example, an injury caused by physical, mechanical, or chemical trauma; (iv) pain; (v) ocular-related neurodegeneration; (vi) memory loss; and (vii) a psychiatric disorder.

Accordingly, in some embodiments, a compound against one of the identified targets, or pathways, can be used to treat or prevent a neurodegenerative disease, disorder, or condition. As used herein, the terms "treat," "treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. The terms "treat," "treating," "treatment," and the like, as used herein can refer to curative therapy, prophylactic therapy, and preventative therapy. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a disease, disorder, or condition, or partial amelioration of one or more symptoms of the disease, disorder, or condition, and can be temporary or permanent. The term "treatment" also is intended to encompass prophylaxis, therapy and cure.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

By "agent" is meant a compound against one of the identified targets, or pathways, or another agent, e.g., a peptide, nucleic acid molecule, or other small molecule compound administered in combination with a compound that modulates the expression or activity of one of the identified targets or pathways. More generally, the term "therapeutic agent" means a substance that has the potential of affecting the function of an organism. Such an agent may be, for example, a naturally occurring, semi-synthetic, or synthetic agent. For example, the therapeutic agent may be a drug that targets a specific function of an organism. A therapeutic agent also may be a nutrient. A therapeutic agent may decrease, suppress, attenuate, diminish, arrest, or stabilize the development or progression of disease, disorder, or condition in a host organism.

The term "administering" as used herein refers to contacting a neuron or portion thereof with a compound against one of the identified targets, or pathways. This term includes administration of the presently disclosed compounds to a subject in which the neuron or portion thereof is present, as well as introducing the presently disclosed compounds into a medium in which a neuron or portion thereof is cultured.

By "neurodegenerative disease, disorder, or condition" is meant a disease, disorder, or condition (including a neuropathy) associated with degeneration or dysfunction of neurons or other neural cells, such as retinal ganglion cells. A neurodegenerative disease, disorder, or condition can be any disease, disorder, or condition in which decreased function or dysfunction of neurons, or loss or neurons or other neural cells, can occur. Particular targets associated with neurodegenerative diseases, disorders, or conditions are disclosed in International PCT Patent Application Publication No. WO2011/050192 to Lewcock et al., published Apr. 28, 2011, which is incorporated herein by reference in its entirety.

As used herein, the term "disorder" in general refers to any condition that would benefit from treatment with a compound against one of the identified targets, or pathways, including any disease, disorder, or condition that can be treated by an effective amount of a compound against one of the identified targets, or pathways, or a pharmaceutically acceptable salt thereof.

Such diseases, disorders, or conditions include, but are not limited to, glaucoma, and neurodegenerative diseases, disorders, or conditions of the nervous systems, such as or associated with amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, Alzheimer's disease, Huntington's disease, Parkinson's disease, Parkinson's-plus diseases, multiple system atrophy, progressive supranuclear palsy, corticobasal degeneration, dementia with Lewy bodies, frontotemporal dementia, demyelinating diseases, Guillain-Barre syndrome, multiple sclerosis, Charcot-Marie-Tooth disease, prion diseases, Creutzfeldt-Jakob disease, Gerstmann-Straussler-Scheinker syndrome (GSS), fatal familial insomnia (FFI), bovine spongiform encephalopathy (BSE), Pick's disease, epilepsy, and AIDS demential complex.

Other neurodegenerative diseases, disorders, or conditions of the nervous systems, such as or associated with alcoholism, Alexander's disease, Alper's disease, ataxia telangiectasia, Batten disease (also known as Spielmeyer-Vogt-Sjogren-Batten disease), Canavan disease, Cockayne syndrome, diabetic neuropathy, frontotemporal lobar degeneration, HIV-associated dementia, Kennedy's disease, Krabbe's disease, neuroborreliosis, Machado-Joseph disease (Spinocerebellar ataxia type 3), wet or dry macular degeneration, Niemann Pick disease, Pelizaeus-Merzbacher Disease, photoreceptor degenerative diseases, such as retinitis pigmentosa and associated diseases, Refsum's disease, Sandhoffs disease, Schilder's disease, subacute combined degeneration of spinal cord secondary to pernicious anemia, Spielmeyer-Vogt-Sjogren-Batten disease (also known as Batten disease), spinocerebellar ataxia (multiple types with varying characteristics), Steele-Richardson-Olszewski disease, and tabes dorsalis.

Examples of ocular-related neurodegeneration include, but are not limited to, glaucoma, lattice dystrophy, retinitis pigmentosa, age-related macular degeneration (AMD), photoreceptor degeneration associated with wet or dry AMD, other retinal degeneration, optic nerve drusen, optic neuropathy, and optic neuritis, such as optic neuritis resulting from multiple sclerosis.

Non-limiting examples of different types of glaucoma that can be prevented or treated according to the presently disclosed subject matter include primary glaucoma (also known as primary open-angle glaucoma, chronic open-angle glaucoma, chronic simple glaucoma, and glaucoma simplex), low-tension glaucoma, primary angle-closure glaucoma (also known as primary closed-angle glaucoma, narrow-angle glaucoma, pupil-block glaucoma, and acute congestive glaucoma), acute angle-closure glaucoma, chronic angle-closure glaucoma, intermittent angle-closure glaucoma, chronic open-angle closure glaucoma, pigmentary glaucoma, exfoliation glaucoma (also known as pseudoexfoliative glaucoma or glaucoma capsulare), developmental glaucoma (e.g., primary congenital glaucoma and infantile glaucoma), secondary glaucoma (e.g., inflammatory glaucoma (e.g., uveitis and Fuchs heterochromic iridocyclitis)), phacogenic glaucoma (e.g., angle-closure glaucoma with mature cataract, phacoanaphylactic glaucoma secondary to rupture of lens capsule, phacolytic glaucoma due to phacotoxic meshwork blockage, and subluxation of lens), glaucoma secondary to intraocular hemorrhage (e.g., hyphema and hemolytic glaucoma, also known as erythroclastic glaucoma), traumatic glaucoma (e.g., angle recession glaucoma, traumatic recession on anterior chamber angle, postsurgical glaucoma, aphakic pupillary block, and ciliary block glaucoma), neovascular glaucoma, drug-induced glaucoma (e.g., corticosteroid induced glaucoma and alphachymotrypsin glaucoma), toxic glaucoma, and glaucoma associated with intraocular tumors, retinal detachments, severe chemical burns of the eye, and iris atrophy. In certain embodiments, the neurodegenerative disease, disorder, or condition is a disease, disorder, or condition that is not associated with excessive angiogenesis, for example, a glaucoma that is not neovascular glaucoma.

Examples of conditions of the nervous system that are secondary to a disease, disorder, condition, or therapy having a primary effect outside of the nervous system include, but are not limited to, peripheral neuropathy or neuralgia caused by diabetes, cancer, AIDS, hepatitis, kidney dysfunction, Colorado tick fever, diphtheria, HIV infection, leprosy, Lyme disease, polyarteritis nodosa, rheumatoid arthritis, sarcoidosis, Sjogren syndrome, syphilis, systemic lupus erythematosus, and amyloidosis.

Examples of pain include, but are not limited to, chronic pain, fibromyalgia, spinal pain, carpel tunnel syndrome, pain from cancer, arthritis, sciatica, headaches, pain from surgery, muscle spasms, back pain, visceral pain, pain from injury, dental pain, neuralgia, such as neurogenic or neuropathic pain, nerve inflammation or damage, shingles, herniated disc, a torn ligament, and diabetes.

Examples of injuries to the nervous system caused by physical, mechanical, or chemical trauma include, but are not limited to, nerve damage caused by exposure to toxic compounds, heavy metals (e.g., lead, arsenic, and mercury), industrial solvents, drugs, chemotherapeutic agents, dapsone, HIV medications (e.g., zidovudine, didanosine, stavudine, zalcitabine, ritonavir, and amprenavir), cholesterol lowering drugs (e.g., lovastatin, indapamide, and gemfibrozil), heart or blood pressure medications (e.g., amiodarone, hydralazine, perhexyline), and metronidazole.

Further examples also include burn, wound, surgery, accidents, ischemia, prolonged exposure to cold temperature (e.g., frost bite), stroke, intracranial hemorrhage, and cerebral hemorrhage. More particularly, traumatic injury or other damage to neuronal cells (e.g., trauma due to accident, blunt-force injury, gunshot injury, spinal cord injury, ischemic conditions of the nervous system such as stroke, cell damage due to aging or oxidative stress, and the like) also is intended to be included within the language "neurodegenerative disease, disorder, or condition." In such embodiments, the presently disclosed methods can be used to treat neuronal damage due to traumatic injury or stroke by preventing death of damaged neuronal cells and/or by promoting or stimulating neurite growth from damaged neuronal cells.

Examples of psychiatric disorders include, but are not limited to, schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, e.g., optic crush experiments, and the like).

In particular embodiments, the subject is suffering from or susceptible to a neurodegenerative disease, disorder, or condition, such as glaucoma, e.g., a subject diagnosed as suffering from or susceptible to a neurodegenerative disease, disorder, or condition. In other embodiments, the subject has been identified (e.g., diagnosed) as suffering from or susceptible to a neurodegenerative disease, disorder, or condition (including traumatic injury) in which neuronal cell loss is implicated, or in which damage to neurites is involved, and for which treatment or prophylaxis is desired.

In certain embodiments, the subject is not suffering, or has not been diagnosed as suffering, from cancer. In certain embodiments, the subject is not suffering, or has not been diagnosed as suffering, from a disorder related to excess angiogenesis. In certain embodiments in which a cell is contacted with a compound against one of the identified targets, or pathways, or a pharmaceutically acceptable salt thereof, the cell is not a neoplastic cell. In certain embodiments of the above aspects, the cell is a mammalian cell, more preferably a human cell.

In some embodiments, the presently disclosed methods produce at least about a 10%, 15%, 20%, 25%, 30%, 35%, 40%, 45%, 50%, 55%, 60%, 65%, 70%, 75%, 80%, 85%, 90%, 95%, or even 100% decrease in cell loss or loss of function relative to cell survival or cell function measured in absence of the tested compound, i.e., a control sample or cell, in an assay. In other embodiments, the compounds and amounts for use in the presently disclosed therapeutic methods produce at least about 10% to 15% increase in neuron count, neuron function, neurite count, neurite total length, or neurite average length relative to absence of the tested compound in an assay.

In any of the above-described methods, the administering of a compound against one of the identified targets, or pathways, can result in at least about a 10%, 15%, 20%, 25%, 30%, 35%, 40%, 45%, 50%, 55%, 60%, 65%, 70%, 75%, 80%, 85%, 90%, 95%, or even 100% decrease in one or more (e.g., 1, 2, 3, 4, 5, 6, 7, 8. 9, or 10) symptoms of a disease, disorder, or condition of the nervous system; a condition of the nervous system that is secondary to a disease, disorder, condition, or therapy having a primary effect outside of the nervous system; injury to the nervous system caused by physical, mechanical, or chemical trauma; pain; ocular-related neurodegeneration; memory loss; or psychiatric disorder, compared to a subject that is not administered the one or more of the agents described herein.

Non-limiting examples of such symptoms include, but are not limited to, tremors, slowness of movement, ataxia, loss of balance, depression, decreased cognitive function, short-term memory loss, long-term memory loss, confusion, changes in personality, language difficulties, loss of sensory perception, sensitivity to touch, numbness in extremities, muscle weakness, muscle paralysis, muscle cramps, muscle spasms, significant changes in eating habits, excessive fear or worry, insomnia, delusions, hallucinations, fatigue, back pain, chest pain, digestive problems, headache, rapid heart rate, dizziness, blurred vision, shadows or missing areas of vision, metamorphopsia, impairment in color vision, decreased recovery of visual function after exposure to bright light, and loss in visual contrast sensitivity.

In any of the above-described methods, the administering of a compound against one of the identified targets, or pathways, results in at least about a 10%, 15%, 20%, 25%, 30%, 35%, 40%, 45%, 50%, 55%, 60%, 65%, 70%, 75%, 80%, 85%, 90%, 95%, or even 100% decrease in the likelihood of developing a disease, disorder, or condition of the nervous system; condition of the nervous system that is secondary to a disease, disorder, condition, or therapy having a primary effect outside of the nervous system; injury to the nervous system caused by physical, mechanical, or chemical trauma; pain; ocular-related neurodegeneration; memory loss; or psychiatric disorder, compared to a control population of subjects that are not administered a compound against one of the identified targets, or pathways.

The administration of one or more agent as described herein may result in at least about a 10%, 15%, 20%, 25%, 30%, 35%, 40%, 45%, 50%, 55%, 60%, 65%, 70%, 75%, 80%, 85%, 90%, 95%, or even 100% decrease in the number of neurons (or neuron bodies, axons, or dendrites thereof) that degenerate in a neuron population or in a subject compared to the number of neurons (or neuron bodies, axons, or dendrites thereof) that degenerate in neuron population or in a subject that is not administered the one or more of the agents described herein.

In some embodiments, the presently disclosed methods include preventing or inhibiting neuron or axon degeneration. The phrases "preventing axon degeneration," "preventing neuron degeneration," "inhibiting axon degeneration," or "inhibiting neuron degeneration" as used herein include: (i) the ability to inhibit or prevent axon or neuron degeneration in patients newly diagnosed as having a neurodegenerative disease or at risk of developing a new neurodegenerative disease; and (ii) the ability to inhibit or prevent further axon or neuron degeneration in patients who are already suffering from, or have symptoms of, a neurodegenerative disease. Preventing axon or neuron degeneration includes decreasing or inhibiting axon or neuron degeneration, which may be characterized by complete or partial inhibition of neuron or axon degeneration. Such prevention or inhibition can be assessed, for example, by analysis of neurological function. Further, the phrases "preventing neuron degeneration" and "inhibiting neuron degeneration" include such inhibition with respect to the entire neuron or a portion thereof, such as the neuron cell body, axons, and dendrites.

The above-listed terms also include in vitro and ex vivo methods. For example, in certain embodiments, the presently disclosed methods are applicable to cell culture techniques wherein it is desirable to prevent neuronal cell death or loss of neuronal function. In vitro neuronal culture systems have proved to be fundamental and indispensable tools for the study of neural development, as well as the identification of neurotrophic factors, such as nerve growth factor (NGF), ciliary trophic factors (CNTF), and brain derived neurotrophic factor (BDNF). One use of certain embodiments of the presently disclosed methods is in cultures of neuronal cells, such as in the use of such cultures for the generation of new neurons and glia. In such embodiments, the cultured cells can be contacted with a compound against one of the identified targets, or pathways, to prevent neuronal cell death or loss of neuronal function. In an exemplary embodiment, the subject method can be used to culture, for example, sensory neurons or, alternatively, motoneurons. Such neuronal cultures can be used as convenient assay systems, as well as sources of implantable cells for therapeutic treatments.

In other examples, the neuron or portion thereof treated according to the presently disclosed methods is ex vivo or in vitro. Accordingly, the presently disclosed compounds can be useful as components of culture media for use in culturing nerve cells in vitro. More particularly, in certain embodiments, the presently disclosed methods can be used to improve the survival or integration of transplanted neuronal cells into a host subject (e.g., through a nerve graft or nerve transplant). Thus, for example, a subject receiving a transplant of neuronal cells can be treated (before, during, or after the transplantation procedure) with compounds according to the presently disclosed methods, to prevent cell death of the transplanted cells (or host cells that may be perturbed during the transplantation procedure), and/or to promote the growth of neurites in the transplanted cells or the host neuronal cells, and thereby promote integration of the transplanted cells into the host nervous system.

The presently disclosed subject matter further provides methods of modulating the growth, cell size, and/or proliferation of a neuron (e.g., cerebellar granule neuron, a dorsal root ganglion neuron, a cortical neuron, or a sympathetic neuron) by contacting a neuron with a compound against one of the identified targets, or pathways.

C. Combination Therapies

In certain embodiments, presently disclosed subject matter also includes combination therapies. Depending on the particular disease, disorder, or condition to be treated or prevented, additional therapeutic agents, which are normally administered to treat or prevent that condition, may be administered in combination with the compounds of this disclosure. These additional agents may be administered separately, as part of a multiple dosage regimen, from the composition comprising a compound against one of the identified targets, or pathways. Alternatively, these agents may be part of a single dosage form, mixed together with the compound against one of the identified targets, or pathways, in a single composition.

By "in combination with" is meant the administration of a compound against one of the identified targets, or pathways, with one or more therapeutic agents either simultaneously, sequentially, or a combination thereof. Therefore, a cell or a subject administered a combination of a compound against one of the identified targets, or pathways, can receive a compound against one of the identified targets, or pathways, and one or more therapeutic agents at the same time (i.e., simultaneously) or at different times (i.e., sequentially, in either order, on the same day or on different days), so long as the effect of the combination of both agents is achieved in the cell or the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound against one of the identified targets, or pathways, and one or more therapeutic agents are administered simultaneously, they can be administered to the cell or administered to the subject as separate pharmaceutical compositions, each comprising either a compound against one of the identified targets, or pathways, or one or more therapeutic agents, or they can contact the cell as a single composition or be administered to a subject as a single pharmaceutical composition comprising both agents. For example, siRNA against MAP2K4 and MAP2K7 may be administered together. As another example, small molecules that inhibit MAP3K12 and MAP3K13 may be administered together. Multiple therapeutic agents may be administered together to modulate one target or multiple targets.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In such combination therapies, the therapeutic effect of the first administered compound is not diminished by the sequential, simultaneous or separate administration of the subsequent compound(s).

A compound against one of the identified targets, or pathways, can be used in therapy in combination with one or more other compounds used to treat a neurodegenerative disease, disorder, or condition. For example, a compound against one of the identified targets, or pathways, can be co-administered in combination with one or more other compounds, for example, at a ratio in the range of 1:1-1:5-5:1, 1:1-1:10-10:1, 1:1-1:25-25:1, 1:1-1:100-100:1, 1:1-1:1000-1000:1 or 1:1-1:10,000-10,000:1, and the like. For example, in the treatment of glaucoma, other anti-glaucoma medicaments can be used in combination with compounds against one of the identified targets, or pathways, including, but not limited to, beta-blockers, including levobunolol (BETAGAN), timolol (BETIMOL, TIMOPTIC), betaxolol (BETOPTIC) and metipranolol (OPTIPRANOLOL); alpha-agonists, such as apraclonidine (IOPIDINE) and brimonidine (ALPHAGAN); carbonic anhydrase inhibitors, such as acetazolamide, methazolamide, dorzolamide (TRUSOPT) and brinzolamide (AZOPT); prostaglandins or prostaglandin analogs such as latanoprost (XALATAN), bimatoprost (LUMIGAN) and travoprost (TRAVATAN); miotic or cholinergic agents, such as pilocarpine (ISOPTO CARPINE, PILOPINE) and carbachol (ISOPTO CARBACHOL); epinephrine compounds, such as dipivefrin (PROPINE); forskolin; or neuroprotective compounds, such as brimonidine and memantine. In certain embodiments, the compound used in combination with a compound against one of the identified targets, or pathways, is not an anti-angiogenic agent, such as a steroid derivative, such as 2-methoxyestradiol or analogs or derivatives thereof. In other embodiments, the additional therapeutic agent can be an antibiotic.

The presently disclosed compounds against one of the identified targets, or pathways, can be optionally combined with or administered in concert with each other or other agents known to be useful in the treatment of the relevant disease, disorder, or condition. Thus, in the treatment of ALS, for example, the presently disclosed compounds can be administered in combination with Riluzole (RILUTEK), minocycline, insulin-like growth factor 1 (IGF-1), and/or methylcobalamin. In another example, in the treatment of Parkinson's disease, the presently disclosed compounds can be administered with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In a further example, in the treatment of Alzheimer's disease, the presently disclosed compounds can be administered with acetylcholinesterase inhibitors (e.g., donepezil, galantamine, and rivastigmine) and/or NMDA receptor antagonists (e.g., memantine). The combination therapies can involve concurrent or sequential administration, by the same or different routes, as determined to be appropriate by those of skill in the art. The presently disclosed subject matter also includes pharmaceutical compositions and kits including combinations as described herein.

In other embodiments, the presently disclosed subject matter includes a combination therapy of administering a compound against one or more of the identified targets, or pathways, in combination with surgery, e.g., surgical relief of intraocular pressure, e.g., via trabeculectomy, laser trabeculoplasty, or drainage implants, and the like.

In still other embodiments, the combination therapy may include administering a compound against one or more of the identified targets along with a transfection reagent, such as Lipofectamine-2000 (L2K), a lipid mediated transfection reagent.

D. Dosage and Mode of Administration

The presently disclosed pharmaceutical compositions can be administered using a variety of methods known in the art depending on the subject and the particular disease, disorder, or condition being treated. The administering can be carried out by, for example, intravenous infusion; injection by intravenous, intraperitoneal, intracerebral, intramuscular, intraocular, intraarterial or intralesional routes; or topical or ocular application.

More particularly, as described herein, the presently disclosed compounds can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art. For example, for ocular administration, an eyedrop formulation can include an effective concentration of a compound against one of the identified targets, or pathways, together with other components, such as buffers, wetting agents and the like. Intravitreal injection also may be employed to administer a presently disclosed compound to the eye.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

For intracerebral use, the compounds can be administered continuously by infusion into the fluid reservoirs of the CNS, although bolus injection may be acceptable. The presently disclosed compounds can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the presently disclosed compounds can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

The presently disclosed pharmaceutical compositions can be manufactured in a manner known in the art, e.g. by means of conventional mixing, dissolving, granulating, dragee-making, levitating, emulsifying, encapsulating, entrapping or lyophilizing processes.

More particularly, pharmaceutical compositions for oral use can be obtained through combination of active compounds with a solid excipient, optionally grinding a resulting mixture, and processing the mixture of granules, after adding suitable auxiliaries, if desired, to obtain tablets or dragee cores. Suitable excipients include, but are not limited to, carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl cellulose; and gums including arabic and tragacanth; and proteins, such as gelatin and collagen; and polyvinylpyrrolidone (PVP:povidone). If desired, disintegrating or solubilizing agents, such as cross-linked polyvinyl pyrrolidone, agar, alginic acid, or a salt thereof, such as sodium alginate, also can be added to the compositions.

Dragee cores are provided with suitable coatings, such as concentrated sugar solutions, which also can contain gum arabic, talc, polyvinylpyrrolidone, carbopol gel, polyethylene glycol (PEG), and/or titanium dioxide, lacquer solutions, and suitable organic solvents or solvent mixtures. Dyestuffs or pigments can be added to the tablets or dragee coatings for product identification or to characterize the quantity of active compound, e.g., dosage, or different combinations of active compound doses.

Pharmaceutical compositions suitable for oral administration include push-fit capsule s made of gelatin, as well as soft, sealed capsules made of gelatin and a coating, e.g., a plasticizer, such as glycerol or sorbitol. The push-fit capsules can contain active ingredients admixed with a filler or binder, such as lactose or starches, lubricants, such as talc or magnesium stearate, and, optionally, stabilizers. In soft capsules, the active compounds can be dissolved or suspended in suitable liquids, such as fatty oils, liquid paraffin, or liquid polyethylene glycols (PEGs), with or without stabilizers. Stabilizers can be added as warranted.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinacious biopharmaceuticals. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacrylate) (Langer et al., J. Biomed. Mater. Res. 15:167, 1981; Langer, Chem. Tech. 12:98, 1982), ethylene vinyl acetate (Langer et al., Id), or poly-D-(−)-3-hydroxybutyric acid (EP 133,988A).

Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy. Such materials can comprise an implant, for example, for sustained release of the presently disclosed compounds, which, in some embodiments, can be implanted at a particular, pre-determined target site.

Pharmaceutical compositions for parenteral administration include aqueous solutions of active compounds. For injection, the presently disclosed pharmaceutical compositions can be formulated in aqueous solutions, for example, in some embodiments, in physiologically compatible buffers, such as Hank's solution, Ringer' solution, or physiologically buffered saline. Aqueous injection suspensions can contain substances that increase the viscosity of the suspension, such as sodium carboxymethyl cellulose, sorbitol, or dextran. Additionally, suspensions of the active compounds or vehicles include fatty oils, such as sesame oil, or synthetic fatty acid esters, such as ethyl oleate or triglycerides, or liposomes. Optionally, the suspension also can contain suitable stabilizers or agents that increase the solubility of the compounds to allow for the preparation of highly concentrated solutions.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

In other embodiments, the pharmaceutical composition can be a lyophilized powder, optionally including additives, such as 1 mM-50 mM histidine, 0.1%-2% sucrose, 2%-7% mannitol at a pH range of 4.5 to 5.5 that is combined with buffer prior to use.

The presently disclosed subject matter also includes the use of a compound against one of the identified targets, or pathways, in the manufacture of a medicament for neuroprotection.

Regardless of the route of administration selected, the presently disclosed compounds, which may be used in a suitable hydrated form, and/or the pharmaceutical compositions are formulated into pharmaceutically acceptable dosage forms such as described below or by other conventional methods known to those of skill in the art.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition (e.g., a disease, condition, or disorder related to loss of neuronal cells or cell function), or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Actual dosage levels of the active ingredients in the presently disclosed pharmaceutical compositions can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular compound employed, or salt thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds against one of the identified targets, or pathways, employed in the pharmaceutical composition at levels lower than that required to achieve the desired therapeutic effect and gradually increase the dosage until the desired effect is achieved. Accordingly, the dosage range for administration will be adjusted by the physician as necessary. It will be appreciated that an amount of a compound required for achieving the desired biological response, e.g., neuroprotective activity, may be different from the amount of compound effective for another purpose.

In general, a suitable daily dose of a compound against one of the identified targets, or pathways, will be that amount of the compound that is the lowest dose effective to produce a therapeutic effect. Such an effective dose will generally depend upon the factors described above. Generally, doses of the compounds against one of the identified targets, or pathways, will range from about 0.0001 to about 1000 mg per kilogram of body weight of the subject per day. In certain embodiments, the dosage is between about 1 µg/kg and about 500 mg/kg, more preferably between about 0.015 mg/kg and about 50 mg/kg. For example, in certain embodiments, a dose can be about 1, 5, 10, 15, 20, or 40 mg/kg/day.

If desired, the effective daily dose of the active compound can be administered as two, three, four, five, six or more sub-doses administered separately at appropriate intervals throughout the day, optionally, in unit dosage forms.

E. Methods for Identifying Neuronal Injury and Associated Genes

The presently disclosed subject matter also provides methods for identifying injury of a neuron, such as a retinal ganglion cell. Injury can be identified by measuring the amount of the target gene, protein, or pathway. For example, if MAP3K12 is the target, the amount of MAP3K12 expression or activity in a cell can be measured and compared to the MAP3K12 expression or activity in an uninjured retinal ganglion cell. Other ways of detecting the amount of MAP3K12 also fall within the scope of the presently disclosed subject matter, such as detection of MAP3K12 outside of the cell (for e.g., by immunological techniques), detection of autoantibodies against MAP3K12, detection of a modified version of the MAP3K12 protein that may be more specific to an injured cell (such as a posttranslational modification), and the like.

Accordingly, in one embodiment the presently disclosed subject matter provides a method for identifying injury of a neuron or retinal pigment epithelial (RPE) cell, the method comprising: measuring the amount of expression or activity of a target protein kinase in the neuron or RPE cell; and determining if the amount of protein kinase expression or activity in the neuron or RPE cell is greater than the amount of protein kinase expression or activity in a control neuron or RPE cell; wherein a determination that the amount of protein kinase expression or activity is greater in the neuron or RPE cell compared to the control neuron or RPE cell is indicative of injury in the neuron. In a particular embodiment, the target protein kinase is selected from the group consisting of MAP3K12, MAP3K13, MAP2K4, and MAP2K7. In another particular embodiment, the neuron and control neuron are retinal ganglion cells or photoreceptor cells.

In another embodiment, a method is provided for identifying a gene encoding a protein kinase associated with neuronal or retinal pigment epithelial (RPE) cell injury or death. In one embodiment, the method comprises: providing a neuron or RPE cell; contacting the neuron or RPE cell with at least one silencing RNA (siRNA) targeting a protein kinase in an amount sufficient to inhibit or increase kinase activity of the protein kinase; and determining whether the neuron or RPE cell survives; wherein a determination that the neuron or RPE cell survives is an indication that the gene encoding the protein kinase is associated with neuronal or RPE cell injury or death. In a particular embodiment, the target protein kinase is selected from the group consisting of MAP3K12, MAP3K13, MAP2K4, and MAP2K7. In another particular embodiment, the neuron is a retinal ganglion cell or a photoreceptor cell.

F. Kits or Pharmaceutical Systems

The presently disclosed compounds and compositions can be assembled into kits or pharmaceutical systems for use in treating or preventing neurodegenerative diseases, disorders, or conditions. In some embodiments, the presently disclosed kits or pharmaceutical systems include a compound against one of the identified targets, or pathways, or pharmaceutically acceptable salts thereof. In particular embodiments, the compounds against one of the identified targets, or pathways, or a pharmaceutically acceptable salt thereof, are in unit dosage form. In further embodiments, the compound against one of the identified targets, or pathways, or a pharmaceutically acceptable salt, can be present together with a pharmaceutically acceptable solvent, carrier, excipient, or the like, as described herein.

In some embodiments, the presently disclosed kits comprise one or more containers, including, but not limited to a vial, tube, ampule, bottle and the like, for containing the compound. The one or more containers also can be carried within a suitable carrier, such as a box, carton, tube or the like. Such containers can be made of plastic, glass, laminated paper, metal foil, or other materials suitable for holding medicaments.

In some embodiments, the container can hold a composition that is by itself or when combined with another composition effective for treating or preventing the condition and may have a sterile access port (for example the container may be an intravenous solution bag or a vial having a stopper pierceable by a hypodermic injection needle). Alternatively, or additionally, the article of manufacture may further include a second (or third) container including a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The presently disclosed kits or pharmaceutical systems also can include associated instructions for using the compounds for treating or preventing a neurodegenerative disease, disorder, or condition. In some embodiments, the instructions include one or more of the following: a description of the active compound; a dosage schedule and administration for treating or preventing a neurodegenerative disease, disorder, or condition; precautions; warnings; indications; counter-indications; overdosage information; adverse reactions; animal pharmacology; clinical studies; and references. The instructions can be printed directly on a container (when present), as a label applied to the container, as a separate sheet, pamphlet, card, or folder supplied in or with the container.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Figure 1:
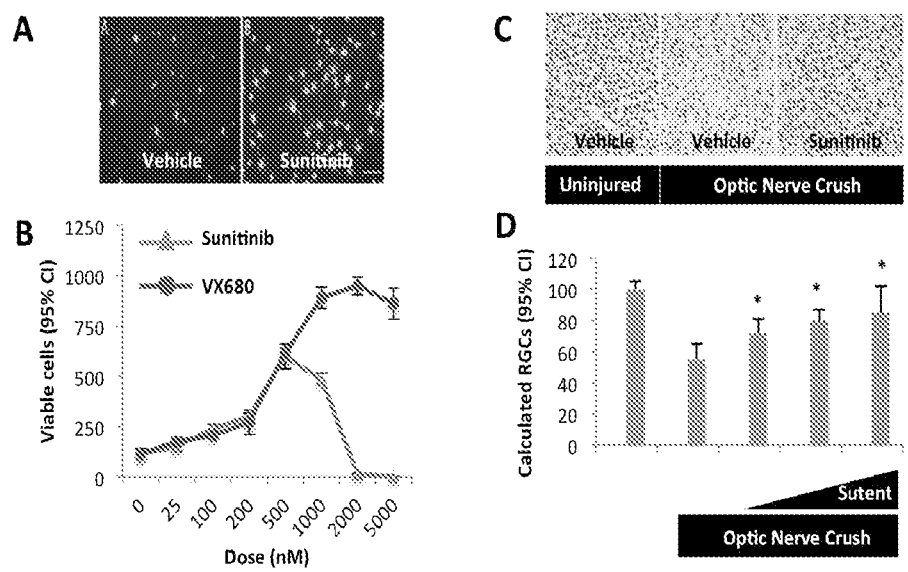

Broad-Spectrum Kinase Inhibitors, Sunitinib and Vx680, are Neuroprotective to Primary RGCS In Vitro and In Vivo To determine the neuroprotective effects of the broad-spectrum kinase inhibitors, sunitinib and VX680, primary RGCs were plated in neurotrophin-depleted media and stained with calcein AM at 72 hours in the absence (vehicle) or presence of 1 µM sunitinib (FIG. 1, Panel A). As can be seen from the higher number of stained cells in the sunitinib sample, the survival of the RGCs was greatly increased when sunitinib was added to the culture.

The survival of primary RGCs in response to increasing doses of sunitinib and VX680 is shown in FIG. 1B. Both sunitinib and VX680 were neuroprotective to primary RGSs. However, at higher doses, VX680 resulted in a greater number of viable cells whereas higher doses of sunitinib resulted in more cell death.

To test the kinase inhibitors in vivo, C57Bl/6 mice were injected intravitreally with 1 µL of drug-eluting microspheres containing 0.125 mg/mL, 0.25 mg/mL, or 0.5 mg/mL of sunitinib, followed by optic nerve crush one week later. RGC survival two weeks after crush was assessed by Nissl staining and counting the nuclei in the ganglion cell layer (GCL). Displaced amacrine cells, whose survival is not affected by optic nerve crush, were assumed to represent 50% of the GCL and thus a 20% reduction in nuclei was interpreted to be a 40% reduction in RGCs. FIG. 1C shows that the addition of sunitinib protected the ganglion cells in the mice as compared to the control (vehicle).

Representative Nissl-stained sections of the GCL show the survival benefit conferred by 0.5 mg/mL sustained-release sunitinib (Sutent) (FIG. 1D).

Example 2

Highly Efficient Knockdown in Primary RGCS Using Magnetofection-Based siRNA Delivery FIG. 2A shows RGCs that were transfected at the time of isolation with 20 nM siGLO-red with (bottom) or without (top) the transfection reagent, NeuroMag and stained for viability at 24 hours with calcein AM. The magnetofection-based siRNA delivery resulted in highly efficient knockdown in primary RGCs as seen by the number of stained cells.

FIG. 2B shows RGCs that were transfected with increasing amounts of siRNA against GAPDH (G) or a nontargeting control (C) and immunoblotted for GAPDH or β-tubulin (control) expression at 48 hours. Transfection with increasing amounts of siRNA resulted in a decreasing amount of GAPDH protein, showing that the siRNA transfection was effective.

Example 3

Screening a Kinase-Enriched siRNA Library in Primary RGCS Identifies a Validated Neuroprotective Target RGCs were plated in a 96-well format and transfected with 2112 siRNAs (20 nM) targeting 704 genes. In addition, each 96-well plate had 6 negative control wells (nontargeting siRNA) and 2 positive control wells (toxic All-Stars #3 siRNA pool; Qiagen). Survival at 72 hours for any given well was normalized to the mean of the 6 control wells (defined as 1.0) (FIG. 3A).

Figure 3:
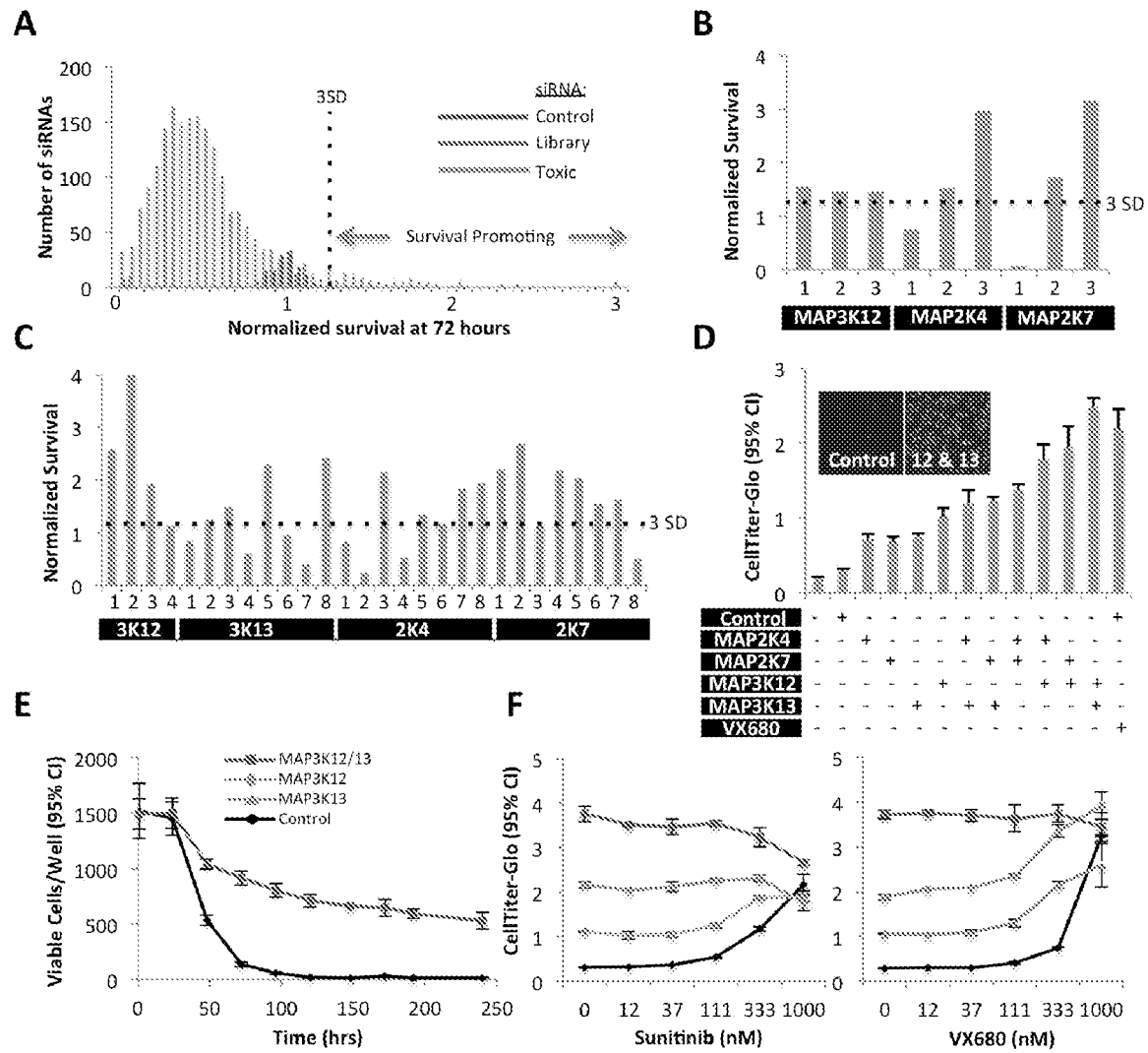

FIG. 3B shows the normalized survival of the top three candidates, defined as genes with 2/3 or 3/3 siRNAs with greater than 1.30 normalized survival (3 SD from mean). These candidates were MAP3K12, MAP2K4, and MAP2K7.

A confirmation screen was performed using an independent set of siGenome or On-Target plus siRNAs (Dharmacon). MAP3K13 was not included in the initial screen but was evaluated here given its high degree of homology to MAP3K12. This screen showed that knock-down of MAP3K12, MAP3K13, MAP2K4, and MAP2K7 promoted RGC survival (FIG. 3C).

To further characterize these candidates, primary RGCs were transfected with siRNAs against the various MAP kinases alone or in combination (10 nM each) and survival was measured at 72 hours with CellTiter-Glo. VX680 (1000 nM) is shown as a reference. A photomicrograph of calcein AM-stained cells at 72 hours transfected with control siRNA or siRNAs targeting MAP3K12 and MAP3K13 is also shown (inset). These results showed that knock-down of MAP3K12, MAP3K13, MAP2K4, and MAP2K7 promoted RGC survival (FIG. 3D).

RGCs transfected with siRNAs against both MAP3K12 and MAP3K13 were followed over time with calcein AM staining. These results showed that siRNA transfection against either MAP3K12, MAP3K13, or a combination of both, resulted in higher survival as compared to the control (FIG. 3E).

RGCs were transfected with 10 nM siRNA against MAP3K12 and MAP3K13 alone or in combination and then plated in 0, 12, 37, 111, 333, and 1000 nM sunitinib (FIG. 3F on left) or VX680 (FIG. 3F on right). Survival at 72 hours is shown. These results showed that addition of sunitinib or VX680 resulted in higher cell viability.

Example 4

MAP3K12/DLK is Upregulated in Response to Retinal Ganglion Cell Injury

RGCs were immunopanned and then plated in 4-well format (250,000 cells per well). At the indicated times, cells were harvested and MAP3K12 protein (FIG. 4A at top) and mRNA (FIG. 4A at bottom) were measured by immunoblotting and quantitative RT-PCR, respectively. GAPDH was used as loading control for both. These results showed that MAP3K12 protein expression was stimulated by optic nerve injury, with only a minimal change in RNA levels, indicating that regulation was post-transcriptional.

C57Bl/6 mice were subjected to unilateral optic nerve crush (3 sec). Five days later, the mice were sacrificed and the retinas were cryosectioned and stained for DAPI as a control (FIG. 4B at top) or MAP3K12/DLK (FIG. 4B at bottom). Shown is a representative section. Addition of MAP3K12/DLK siRNA resulted in increased retinal ganglion cell viability.

Example 5

Knock-Down of MAP3K12/DLK Promotes RGC Survival and Neurite Outgrowth

RGCs were transfected with MAP3K12/DLK siRNA and cultured for 14 days. The cells were then stained with calcein AM. Results demonstrate that knock-down of MAP3K12/DLK promotes RGC survival and neurite outgrowth. Cells without knock-down of MAP3K12/DLK would essentially be dead at this time point.

Example 6

Knock-Down of Other Protein Kinases Promotes RGC Survival and Neurite Outgrowth

Other protein kinases were also tested in this screen. RGCs were transfected with each siRNA and cultured for 14 days. The cells were then stained with calcein AM. Results demonstrated that knock-down of a number of protein kinases promotes RGC survival and neurite outgrowth. The protein kinases tested and found to promote RGC survival were MAP3K12, MAP3K13, MAP3K14, MAP2K7, MAP2K4, LYN, PLK3, PFKP, MARK3, MARK2, TAOK1, IKBKB, BRSK2, PBK, PRKCH, TESK1, Csnk1e, Oxsr1, Tgfbr2, Mapk10, PFTK1, ERN2, AK2, HSPB8, FRAP1, DGUOK, ERN1, STK32B, PIK3C2G, BCR, DYRK1A, DYRK1B, PNCK, EIF2AK1, PKD2L1, NRK, Endothelin Receptor Type B, and TLK2.

The kinases listed, when inhibited by siRNA treatment, substantially altered RGC neuron survival, indicating that they and the pathways they regulate are targets for therapeutic intervention. This may be by activating or inhibiting the target gene by administration of siRNA or other gene expression or activity modifying agents.

Example 7

Functional Genomic Screening Identifies MAP3K12/DLK as a Mediator of Retinal Ganglion Cell Death To identify kinases that could serve as novel targets for neuroprotective glaucoma therapy, the entire mouse kinome was screened for kinases whose inhibition promotes RGC survival. For this screen, a high-throughout method was developed for transfecting primary RGCs with small interfering RNA oligonucleotides (siRNAs) and coupled with a quantitative assay of RGC survival. Results of the screen are presented, which identified the dual leucine zipper kinase (DLK; MAP3K12) as being important in INK activation and RGC cell death following injury. Moreover it is demonstrated, using a conditional knockout approach, that inhibition of MAP3K12/DLK signaling can promote RGC survival in vivo, and also identify a small molecule kinase inhibitor that protects RGC somata and axons in a rodent model of glaucoma.

Materials and Methods

Statistical Analysis. All statistical analyses were performed with the unpaired Mann-Whitney-Wilcoxon test.

Rat optic nerve transection. The optic nerve was exposed by a partial peritomy and intraorbital dissection of the extraocular muscles, and then transected with a 25-gauge needle. 4-Di-10-ASP was then applied to the proximal nerve stump. Care was taken to avoid vascular injury during the transection, and retinal perfusion was examined after nerve transection. Two weeks after transection, rats were sacrificed and enucleated. Retinas were flatmounted, imaged with Zeiss LSM 510 META confocal microscope with a Zeiss Plan-Apochromat 20×/0.75 NA objective. Images were taken from four fields of 230 mm×230 mm squares located 2 mm superior, inferior, temporal, and nasal to the optic disc. The number of 4-Di-10-ASP-labeled cells with RGC morphology was quantified. Imaging and quantification of RGC survival was performed in a masked fashion.

Rat laser-induced ocular hypertension. Intraocular pressure (TOP) was unilaterally elevated by laser treatment of the trabecular meshwork as previously described (Levkovitch-Verbin et al. Investigative Ophthalmology & Visual Science 43:402-410, 2002). Briefly, 6-week old Wistar male rats were anesthetized with ketamine/xylazine. On two consecutive weeks, 40-50 532 nm diode laser spots were applied to the prelimbal region (50 μm diameter, 600 mW power and 0.6 seconds duration). Under anesthesia, the IOP of laser treated and fellow eyes was measured with TonoLab one and three days after laser treatment. Four weeks following laser treatment, toluidine blue-stained optic nerves were imaged and the number of axons counted. The laser treatment and acquisition of optic nerve images were performed in a masked fashion. RGC somata were measured by Brn3 staining of retina sections. The number of Brn3-positive cells was normalized by the number of DAPI-stained cells in GCL on the same sections.

Mouse intravitreal injection and optic nerve crush. 3-month old male C57BL/6 and Dlk floxed mice (BL/6 background) were anesthetized with ketamine/xylazine and intravitreally injected with 10¹⁰ DNA-containing particles of capsid-mutant (Y444, 500, 730F) AAV2 expressing Cre recombinase from the chicken β-actin promoter. 7 days later, optic nerve was surgically exposed and crushed with Dumont N7 self-closing forceps 1 mm behind the globe for 3 seconds. 10 days following nerve crush, eyes were enucleated, fixed and surviving RGC was immunostained for βIII-tubulin and Brn3. The retinas were then imaged with a Nikon Eclipse TE2000-5 fluorescence microscope and Planfluor 40×/0.6 objective. Images were acquired from the four fields in the superior, inferior, temporal and nasal quadrants 1 mm from the optic disc. RGCs were counted manually from each image.

In a separate cohort of animals, optic nerves and retinas were sectioned and stained for phospho-JNK and c-Jun, respectively, 24 hours after optic nerve crush. Intravitreal injection, optic nerve crush, immunofluorescence and RGC counting were performed in a masked fashion.

Reagents. Antibodies: Phospho-JNK, Thr183/Tyr185 (4671); JNK (9258); c-Jun (9165); Phospho-MKK7 (4171) and MKK7 (4172) (Cell Signaling Technology); monoclonal anti-alpha-tubulin antibody (T6074) (Sigma); mouse neuronal class βIII tubulin (TUJ1) (Covance); goat polyclonal Brn3 (C-13); and rabbit anti-Cre (Novus).

Retinal Ganglion Cell Purification, Culture, Screening, and Imaging. All animal use was in accordance with the Association for Research in Vision and Opthalmology (ARVO) Statement for the Use of Animals, following animal protocols approved by the Institutional Animal Care and Use Committee at Johns Hopkins University. Retinas were isolated from postnatal 0-5-d mice and dissociated with papain. Microglia were immunodepleted with anti-CD11b conjugated Dynabeads (Life Technologies). The suspension of retinal cells was immunopanned on plates preconjugated with anti-Thy1.2 antibody (Serotec, MCA028) and goat antimouse IgM (Jackson Immunoresearch) at room temperature (RT). After washing, retinal ganglion cellS (RGCs) were released from the plate by a cell lifter, counted, and seeded at a density of 10,000 per well in 96-well plates in the media composed of Neurobasal (Life Technologies), B27, N2 supplement, Lglutamine, and penicillin/streptomycin. After a 72-h culture at 37° C., RGCs were stained with calceinAM (acetomethoxy derivate of calcein), ethidium homodimer, and Hoechst 33342. Images were taken from portions of each well with a Cellomics ArrayScan VTI HCS Reader (Thermo Fisher), and cell survival was quantified using the Cellomics Neuronal Profiling bioapplication. As indicated, RGC viability was alternatively measured by Cell-Titer-Glo (Promega) luminescence.

For siRNA-based screening, the siRNAs from the Sigma Mission Mouse Kinome library were complexed with NeuroMag (Oz Biosciences) at a final concentration of 20 nM. RGCs were then reverse transfected on a stationary magnet and assayed for survival 72 h later using CellTiter-Glo (Promega). Confirmatory siRNAs were obtained from both Dharmacon and Ambion. Adenoviruses expressing wild-type or kinase-dead dual leucine zipper kinase, GFP, or Cre were added to RGCs at a multiplicity of infection of 100-1000.

Rat Intravitreal Injections. Six-week old male Wistar rats were anesthetized with ketamine/xylazine. A partial peritomy was made to expose the sclera. The injection site was approximately at the ora serrata, and the injection glass pipet was angled toward the optic disk to avoid lens injury. Five microliters (10 ng) of PLGA microspheres were injected with a glass pipet and Hamilton syringe.

Electrophysiology. Recordings were made by using the whole-cell patch-clamp technique in both current- and voltage-clamp modes with an Axopatch 200B (Molecular Devices). Data were low-pass filtered at 1 kHz (Bessel) and sampled at 10 kHz. A liquid junction potential of −2 mV has been corrected, and the resting potential was estimated to be −62±2.2 mV (mean±SEM; n=13). The recording pipette was filled with the following intracellular solution (in mM): 100 K-gluconate, 50 KCl, 20 Hepes, 10 EGTA, 5 MgCl$_2$, 2 ATP, 0.1 GTP, pH adjusted to 7.33 with KOH. The cells were continuously perfused with (in mM) 140 NaCl, 5 KCl, 1 MgCl$_2$, 2.5 CaCl$_2$, 10 glucose, 10 Hepes, pH 7.4, with NaOH.

Production of Adeno-Associated Virus Vectors. Adeno-associated virus vector was produced by the 2-plasmid, cotransfection method with modifications (Zolotukhin et al., *Methods* 28(2):158-167, 2002).

RNAi-Based Screen Identifies MAP3K12/DLK

Figure 6:
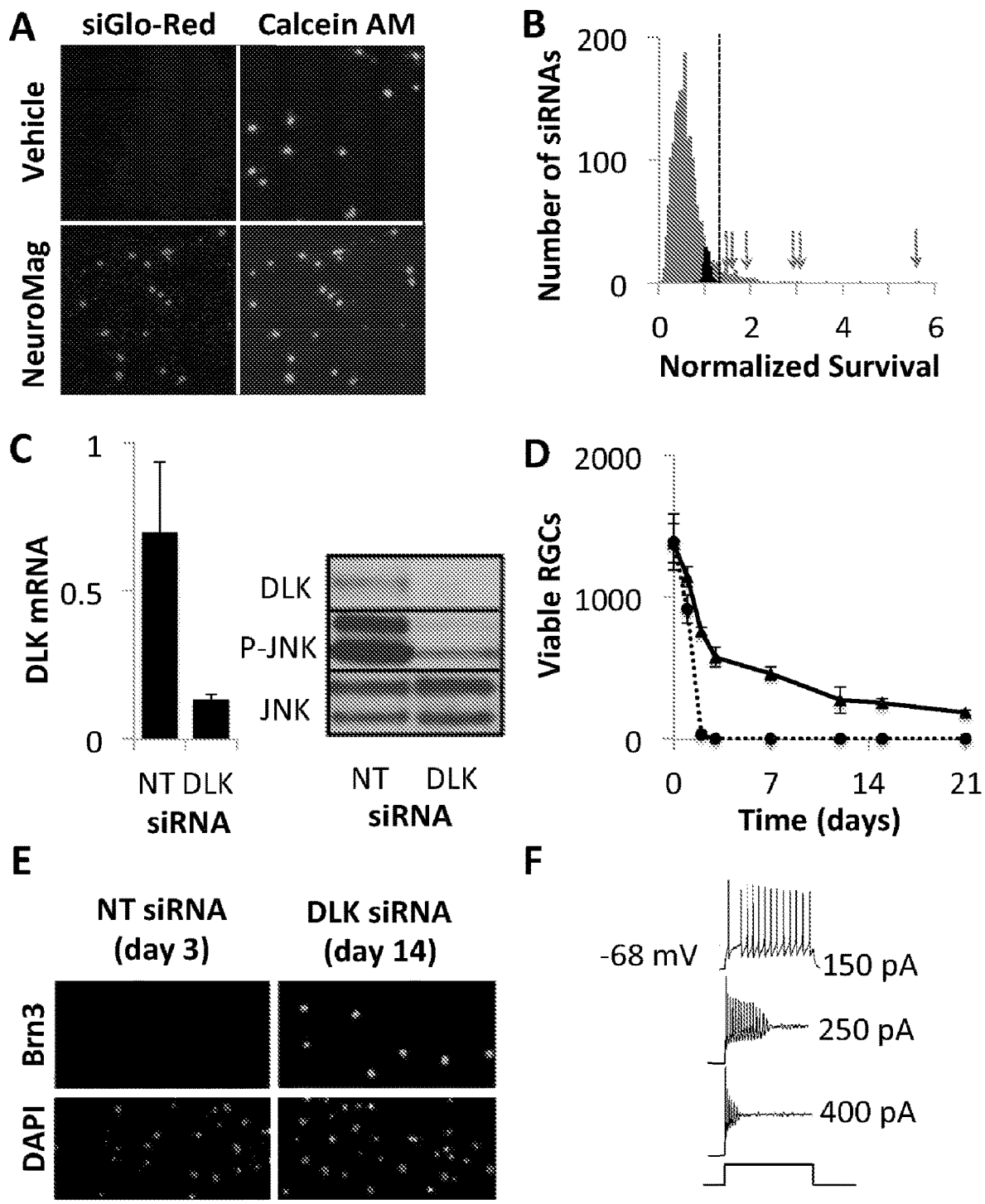

In order to develop a biologically relevant RGC survival assay, primary RGCs were immunopanned from perinatal mice (Barres et al. *Neuron* 1:791-803, 1988). Despite the inherent challenges in the use of primary neurons, they are more likely than established cell lines to be predictive of in vivo efficacy (Sharma et al. *Meth Enzymol* 506:331-360, 2012). Individually inhibiting the function of each kinase in the genome required an efficient method for siRNA delivery to the primary RGCs. Since traditional transfection procedures were either toxic or minimally effective with RGCs, a magnetic nanoparticle-based reagent (NeuroMag) was adapted for high-efficiency, high-throughput siRNA delivery (FIG. 6A). NeuroMag-based transfection resulted in consistent and efficient suppression of target gene expression in unselected RGC populations (FIG. 7).

Using this approach, an arrayed library of 1869 siRNAs was screened against 623 kinases, providing three-fold coverage of the mouse kinome, for the ability to promote the survival of RGCs grown in neurotrophin-deficient media (FIG. 6B). To minimize the number of false-positive leads resulting from off target silencing, a conservative approach was taken to focus only on kinases for which all three siRNAs were protective. Indeed, only two kinases met this criterion, MAP3K12/DLK and its only known substrate, mitogen-activated protein kinase kinase 7 (MKK7) (Merritt et al. *J. Biol. Chem.* 274:10195-10202, 1999). Secondary testing, using an independent set of siRNA with distinct targeting sequences, confirmed that both kinases were the relevant targets (FIG. 8A). Supporting the biological relevance of this finding, MKK7 and its homolog, MKK4, are the canonical activators of JNK1-3 (Tournier et al. *Proceedings of the National Academy of Sciences of the United States of America* 94:7337-7342, 1997), key regulators of RGC cell death (Sun et al. *Mol. Vis.* 17:864-875, 2011; Ribas et al. Neuroscience 180:64-74, 2011; Bessero et al. *J. Neurochem.* 113:1307-1318; Fernandes et al. *Neurobiology of Disease* 46(2):393-401, 2012). As an additional validation that our siRNA result was specifically due to MAP3K12/DLK pathway inhibition, RGCs were isolated from mice containing a floxed allele of Dlk (Miller et al. *Nat. Neurosci.* 12:387-389, 2009) or wildtype controls and then transduced with adenovirus expressing the P1 bacteriophage Cre recombinase or a GFP control. Similar to the results with RNA interference, genetic deletion of MAP3K12/DLK led to increased RGC survival (FIG. 8B).

MAP3K12/DLK Downregulation Promotes Long-Term Survival and Function of RGCs In Vitro The kinetics of RGC cell death following MAP3K12/DLK knockdown were studied Immunopanned RGCs were transfected with Dlk siRNA, or a nontargeting control, and followed over time. By 24 hours, Dlk siRNA efficiently reduced MAP3K12/DLK expression at both the mRNA and protein levels. Consistent with MAP3K12/DLK being a major activator of JNK in injured RGCs, MAP3K12/DLK knockdown inhibited JNK phosphorylation, indicating attenuation of downstream JNK signaling (FIG. 6C). By 48 hours there was a clear survival effect (FIG. 6D). While there were very few live control cells, RGCs transfected with Dlk siRNA had greater than 50% viability. The pro-survival effect of MAP3K12/DLK inhibition persisted for at least 3 weeks. Dlk mRNA levels stayed low throughout this period, consistent with reports that siRNA knockdown in post-mitotic neurons can be long-lived (Tanaka et al. *Neurochem. Res.* 36:1482-1489, 2011; Tanaka et al. *J. Neurosci. Methods* 178:80-86, 2009).

Axonal injury typically reduces the expression of many RGC specific markers secondary to the downregulation of the Brn3 family of transcription factors (Yang et al. *Investigative Opthamology & Visual Science* 48:5539-5548, 2007). However, in RGCs with MAP3K12/DLK knockdown, Brn3 continued to be expressed (FIG. 6E). This showed that MAP3K12/DLK may be a relatively upstream injury signal and that injured RGCs, in the absence of MAP3K12/DLK signaling, maintain characteristics of uninjured RGCs. At the functional level, patch-clamp recordings showed that RGCs kept alive for two weeks with Dlk siRNA continue to generate action potentials in response to depolarizing current (FIG. 6F).

MAP3K12/DLK Inhibition Promotes RGC Survival In Vivo Following Optic Nerve Injury To test the role of MAP3K12/DLK on RGC survival in vivo, the mouse optic nerve crush model was used. In response to axonal injury, 50-75% of RGCs die by two weeks (Li et al. *Investigative Ophthalmology & Visual Science* 48:5539-5548, 2007). Mice carrying a floxed allele of Dlk (Dlkfl/fl) were injected intravitreally with a self-complementary, capsid-modified adenoassociated virus 2 (AAV2)(Petrs-Silva et al. *Mol. Ther.* 17:463-471, 2009; Petrs-Silva et al. *Mol. Ther.* 19:293-301) expressing Cre. Injection of the AAV2-Cre resulted in Cre expression in nearly 100% of RGCs (FIG. 9A). One week after injection, to allow sufficient time for Cre-mediated deletion of Dlk (FIG. 9B), optic nerve crush was performed. Ten days later, retinal flatmounts were prepared and stained for the RGC-specific marker βIII-tubulin and the number of surviving RGCs was determined. Compared to control animals (Dlk+/+ mice injected with AAV2-Cre or Dlkfl/fl mice in the absence of Cre), Dlkfl/fl mice injected with AAV2-Cre showed a 75% reduction in RGC loss (FIG. 9C). This increase in RGC survival was associated with decreased JNK phosphorylation (FIG. 9D) and c-Jun expression (FIG. 9E), markers of JNK signaling (Derijard et al. *Cell* 76:1025-1037, 1994; Angel et al. *Cell* 55:875-885, 1988). These results show that MAP3K12/DLK may be the primary kinase responsible for JNK pathway activation following axonal injury.

Axonal Injury Upregulates MAP3K12/DLK Expression Through a Posttranscriptional Mechanism The mechanism of MAP3K12/DLK regulation was examined next. Surprisingly, and unlike other members of the JNK cascade, MAP3K12/DLK protein is undetectable in uninjured RGCs both in vitro and in vivo (FIG. 10A, FIG. 10B-left panel). However, culturing RGCs in vitro (which necessarily involves axotomy and cell injury) and transection in vivo both lead to robust upregulation of MAP3K12/DLK protein (FIG. 10A, FIG. 10B-right panel). In vitro, MAP3K12/DLK protein levels increased more than 10-fold within 18 hours from the initiation of cell culture. In contrast, Dlk transcript levels remained relatively constant during this period (FIG. 10A), indicating that increased translation and/or decreased protein turnover must underlie the mechanism of MAP3K12/DLK upregulation. In *D. melanogaster*, Wallenda/DLK is post-translationally regulated by the E3 ubiquitin ligase Highwire (Collins et al. Neuron 51:57-69, 2006; Xiong et al. *J. Cell Biol.* 191:211-223, 2010). However, mice with a brain-specific conditional knockout of Phr 1 (the vertebrate Highwire homolog) show no difference in the overall brain levels of MAP3K12/DLK protein (Bloom et al. *Genes Dev.* 21:2593-2606, 2007). Furthermore, knockdown of PHR1 in RGC cultures did not affect MAP3K12/DLK levels, showing that either PHR1 regulates MAP3K12/DLK levels only in certain settings/neuronal subtypes or that MAP3K12/DLK levels in vertebrates are regulated by another as yet unidentified protein.

Since MAP3K12/DLK downregulation promotes RGC survival, the complementary hypothesis that increased MAP3K12/DLK expression can trigger RGC cell death was tested. Adenovirus was used to overexpress GFP, MAP3K12/DLK or a kinase-dead (KD) version of MAP3K12/DLK (K185R) (Robitaille et al. *Cell Death Differ.* 11:542-549, 2004). Primary RGCs were transduced and survival measured 48 hours later. Consistent with the present model, wildtype MAP3K12/DLK overexpression hastened cell death, while overexpression of K185R MAP3K12/DLK, which functioned as a dominant-negative mutant as assessed by JNK phosphorylation, actually promoted RGC survival (FIG. 10C).

Discussion

Large-scale RNAi-based phenotypic screens in lower organisms have successfully identified genes involved in the rescue of neuronal degeneration (Bhattacharya et al. *J. Neurosci.* 32:5054-5061, 2012; Dimitriadi et al. *PLoS Genet.* 6:e1001172, 2010; Schulte et al. *PLoS ONE* 6:e23841, 2011). Parallel screens utilizing primary vertebrate neurons, however, have been more difficult due to the challenges working with and transfecting primary neuronal cell cultures. Using a magnetic nanoparticle-based method, easily compatible with automation, these challenges were overcome to perform the first kinome-wide survival screen using a disease-relevant primary neuron. This global and unbiased approach led to the identification of MAP3K12/DLK signaling as a key cell death pathway in RGC degeneration. Moreover, it established the proof-of-principle for a whole-genome scan in primary RGCs to identify additional potential neuroprotective pathways and drug targets.

Although the JNK pathway may be involved in both traumatic and glaucomatous models of optic neuropathy (Sun et al. Mol. Vis. 17:864-875, 2011; Ribas et al. *Neuroscience* 180:64-74, 2011; Bessero et al. *J. Neurochem.* 113:1307-1318; Fernandes et al. *Neurobiology of Disease* 46(2):393-401, 2012), the mechanism by which axonal injury leads to JNK activation in RGC cell bodies has been unclear. The present results show that MAP3K12/DLK may be the as-yet-unidentified trigger for JNK activation and cell death in injured RGCs.

The present results, in addition to implicating MAP3K12/DLK in neurodegenerative RGC cell death, also show that MAP3K12/DLK may be important in other forms of CNS neurodegenerative cell loss. The finding that MAP3K12/DLK is required for the death of freshly cultured RGCs indicates that MAP3K12/DLK does more than just retrograde axonal injury signaling because the cell preparation and purification process completely strips the cells of detectable axonal and dendritic processes. Upregulated MAP3K12/DLK may contribute to the cell death process directly within the RGC's cell body.

The JNK signal transduction pathway consists of multiple branches that feed into one or more of the JNKs (Weston et al. *Curr. Opin. Cell Biol.* 19:142-149, 2007). Although a possible approach to RGC neuroprotection is to directly block the pathway downstream with small molecule JNK inhibitors, such non-specific inhibition of the entire pathway may not be an ideal therapeutic strategy since JNK signaling has a number of important physiologic roles, such as tumor suppression (Davies & Tournier *Biochem. Soc. Trans.* 40:85-89, 2012). However, the present finding that the MAP3K12/DLK branch is the major pathway leading to proapoptotic JNK activation following RGC injury makes possible a more fine-tuned and specific approach.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

International PCT Patent Application Publication No. WO2010/017541, to Zack et al., for Compositions and Methods for Treatment of Neurodegenerative Disease, published Feb. 11, 2010;

International PCT Patent Application Publication No. WO2011/119777 to Zack et al., for Compositions and Methods for Treatment of Neurodegenerative Disease, published Sep. 29, 2011;

International PCT Patent Application Publication No. WO2011/050192 to Lewcock et al., for Modulation of Axon Degeneration, published Apr. 28, 2011.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for inhibiting retinal ganglion cell injury or death, the method comprising: contacting the retinal ganglion cell with a first short interfering RNA (siRNA) that inhibits the expression or activity of Mitogen-Activated Protein Kinase Kinase Kinase 12 (MAP3K12) and a second siRNA that inhibits the expression or activity of Mitogen-Activated Protein Kinase Kinase Kinase 13 (MAP3K13).

2. The method of claim 1, wherein the retinal ganglion cell is contacted with the first siRNA and second siRNA ex vivo or in vivo.

3. The method of claim 2, wherein the method further comprises grafting or implanting the retinal ganglion cell into a subject after contacting the cell with the first siRNA and the second siRNA.

4. The method of claim 3, wherein the retinal ganglion cell is in a pharmaceutically acceptable carrier.

5. The method of claim 1, wherein inhibiting retinal ganglion cell injury or death treats an ocular neurodegenerative disease.

6. The method of claim 5, wherein the ocular neurodegenerative disease is selected from the group consisting of glaucoma, retinal degeneration, and age-related macular degeneration.

* * * * *